United States Patent [19]
Correa

[11] Patent Number: 6,023,939
[45] Date of Patent: Feb. 15, 2000

[54] FAN AND MOTOR ASSEMBLY FOR AN AIR CONDITIONER

[75] Inventor: Juan Carlos Carne Correa, Rio Grande do Sul, Brazil

[73] Assignee: Carrier Corporation, Syracuse, N.Y.

[21] Appl. No.: 09/101,587

[22] PCT Filed: Dec. 11, 1996

[86] PCT No.: PCT/BR96/00059

§ 371 Date: Jul. 13, 1998

§ 102(e) Date: Jul. 13, 1998

[87] PCT Pub. No.: WO98/26185

PCT Pub. Date: Jun. 18, 1998

[51] Int. Cl.$^7$ .................................................. F25D 23/12
[52] U.S. Cl. ................................. 62/298; 62/262; 416/178
[58] Field of Search ....................... 62/262, 298; 416/178

[56] References Cited

U.S. PATENT DOCUMENTS

| | | | |
|---|---|---|---|
| 4,044,570 | 8/1977 | Ono Minoru et al. | 62/419 |
| 4,102,148 | 7/1978 | Matthews et al. | 62/77 |
| 5,203,400 | 4/1993 | Tsunekawa et al. | 165/59 |
| 5,295,531 | 3/1994 | Tsunekawa et al. | 165/48.1 |
| 5,415,011 | 5/1995 | Gilmore et al. | 62/262 |
| 5,461,880 | 10/1995 | Bolton et al. | 62/298 |
| 5,732,565 | 3/1998 | Ramakrishnan et al. | 62/298 |

FOREIGN PATENT DOCUMENTS 4334124A  9/1994  Germany .

*Primary Examiner*—Henry Bennett
*Assistant Examiner*—Mark Shulman

[57] ABSTRACT

A subassembly of an electric motor and a fan for use in an air conditioner includes a centrifugal fan adapted for rotation about a longitudinal axis. The fan has an open inlet end at one longitudinal end thereof and convex closed end partition defining a cup-shaped space at the other axial end thereof. The fan motor includes a housing having an axial length and a width and a drive shaft extending from one axial end thereof. The closed end partition of the centrifugal fan has a centrally disposed axially extending opening therethrough through which the drive shaft of the motor is adapted to be received and operatively attached. The width of the motor housing and the cup-shaped space are sized to allow a substantial portion of the axial length of the motor housing to be received within said cup-shaped space when the drive shaft is operably attached to the partition. The evaporator module for an air conditioner includes a structural indoor housing having a rear wall which is provided with an axial opening therein which is adapted to receive at least a portion of the evaporator fan motor therein. The rear wall further includes fan support structure associated therewith, which defines the opening. The fan support structure is adapted to extend into said cup-shaped space to engage the fan support structure to support the fan and motor subassembly in its desired operative position with respect to the housing.

7 Claims, 30 Drawing Sheets

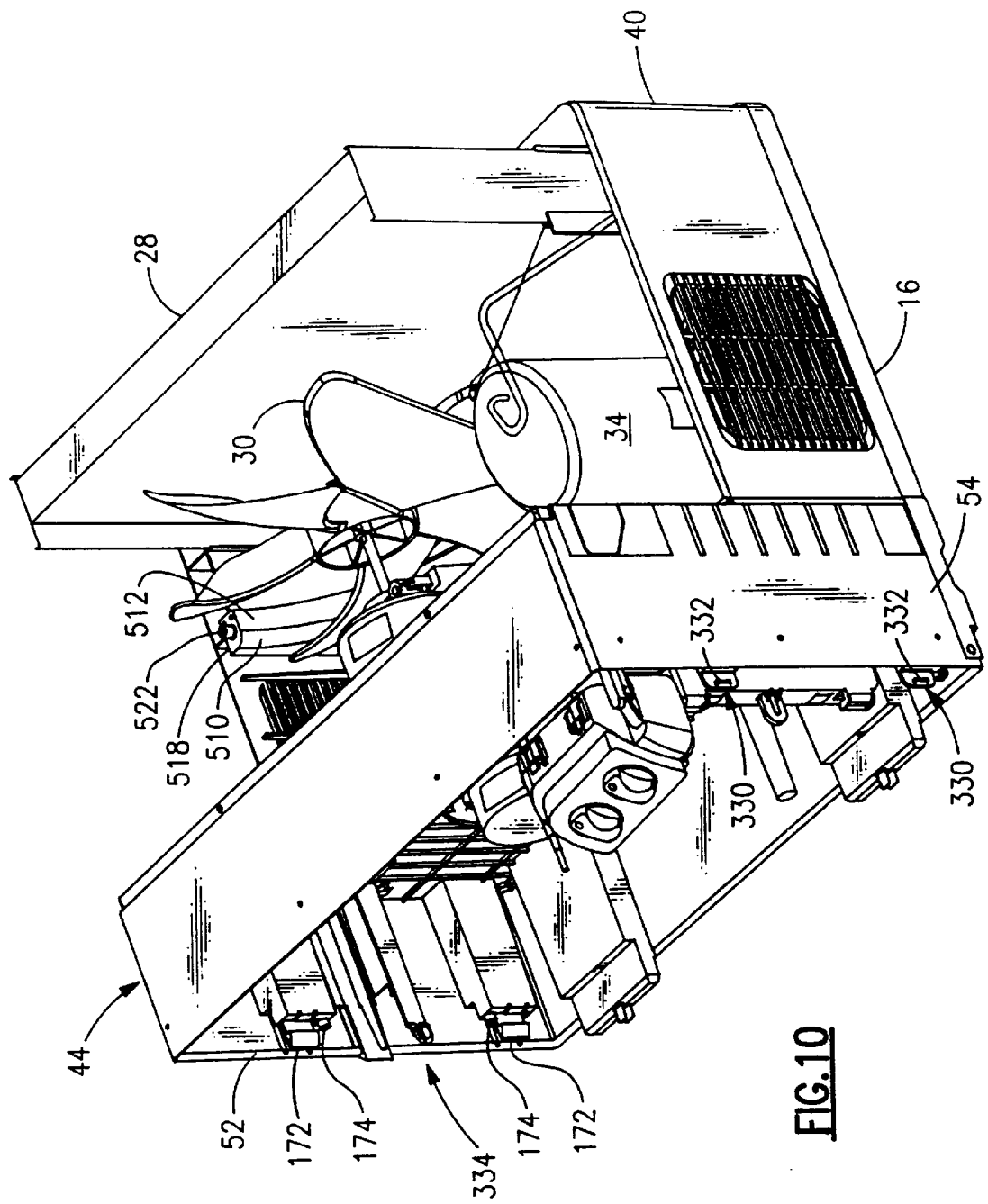

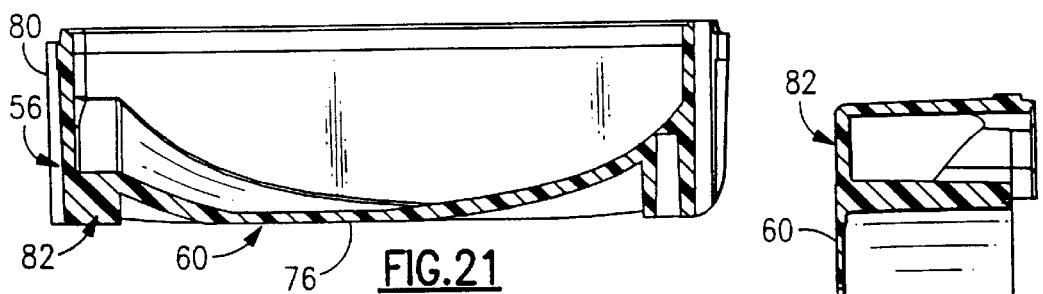
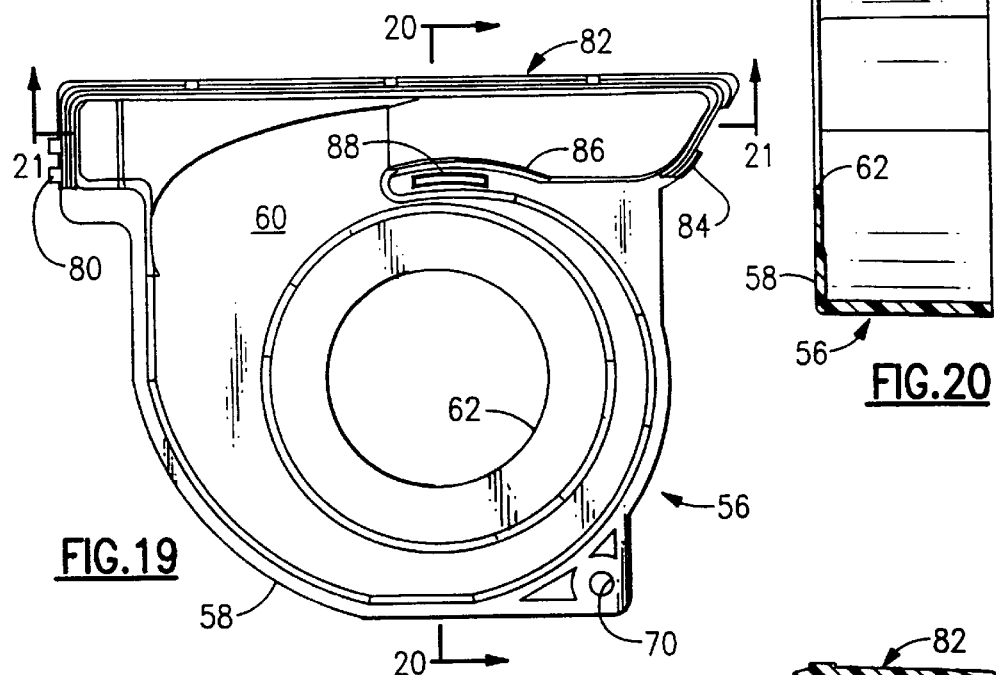
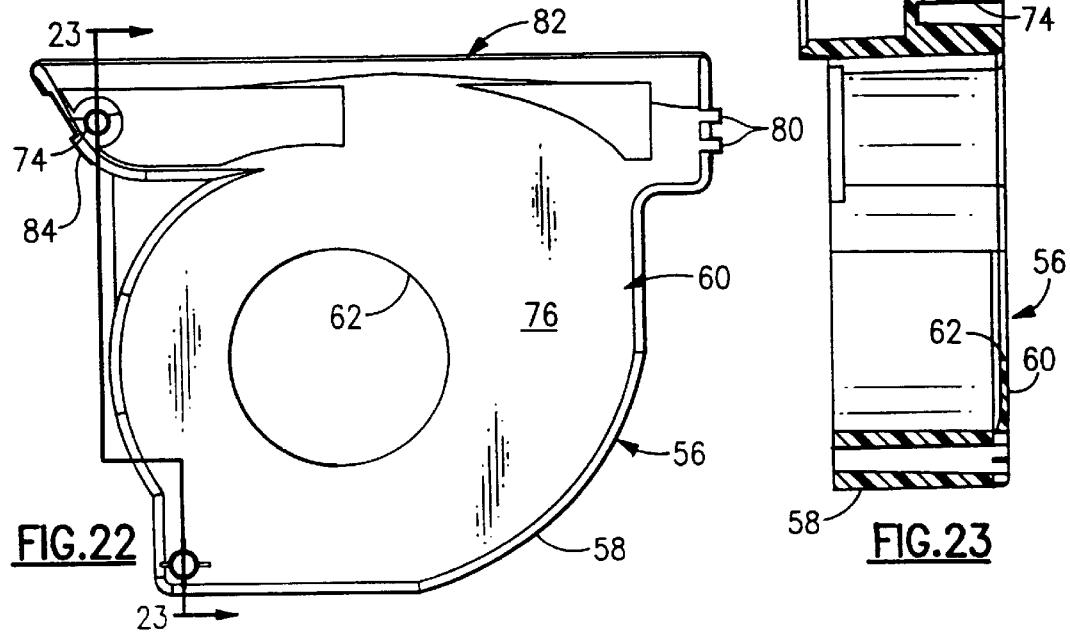
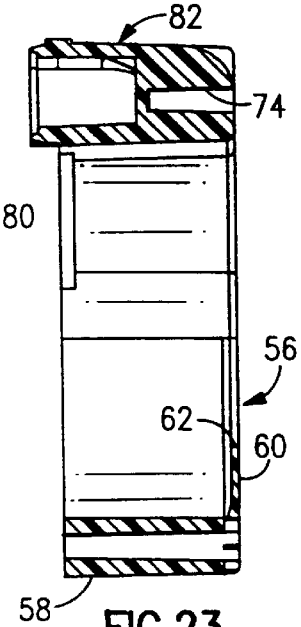

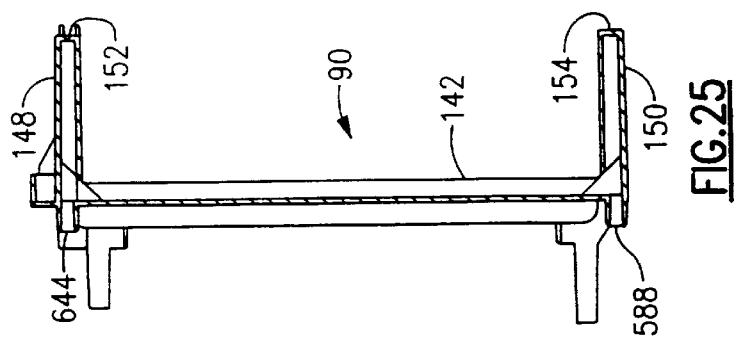
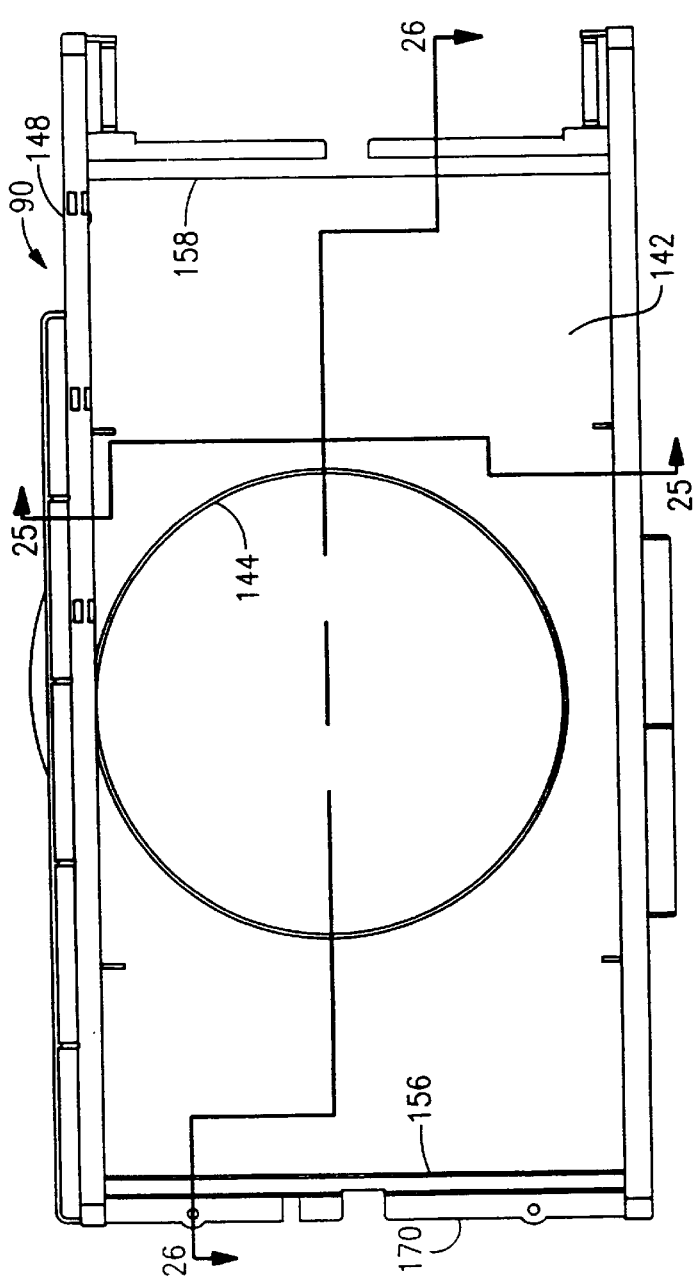
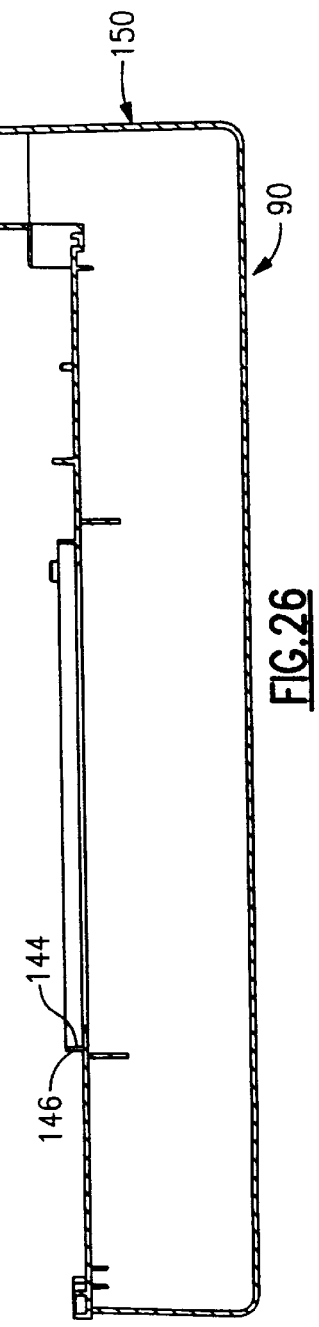

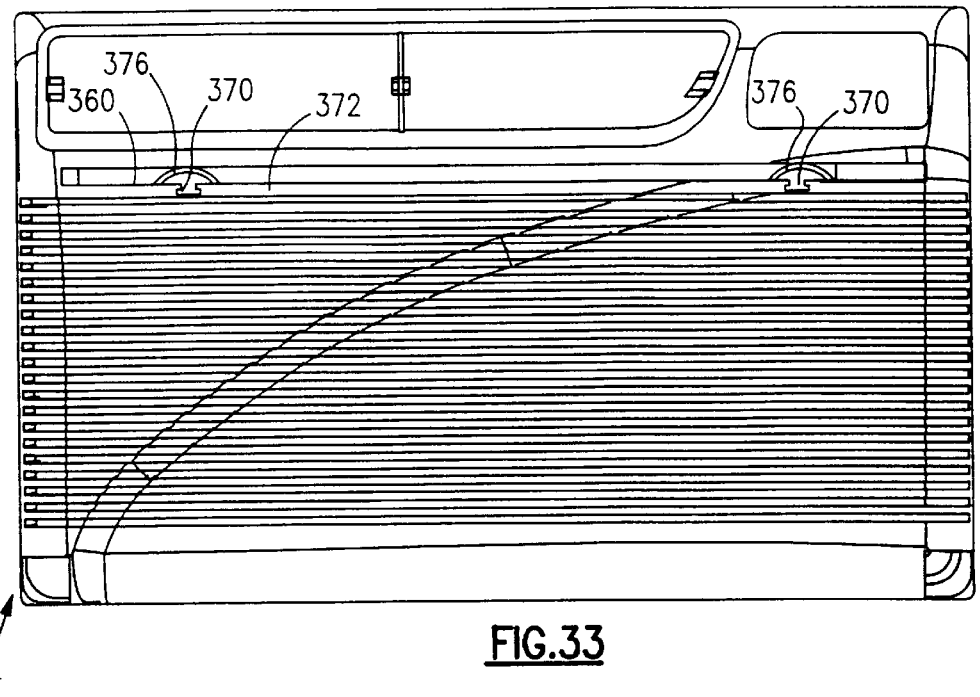
FIG.33
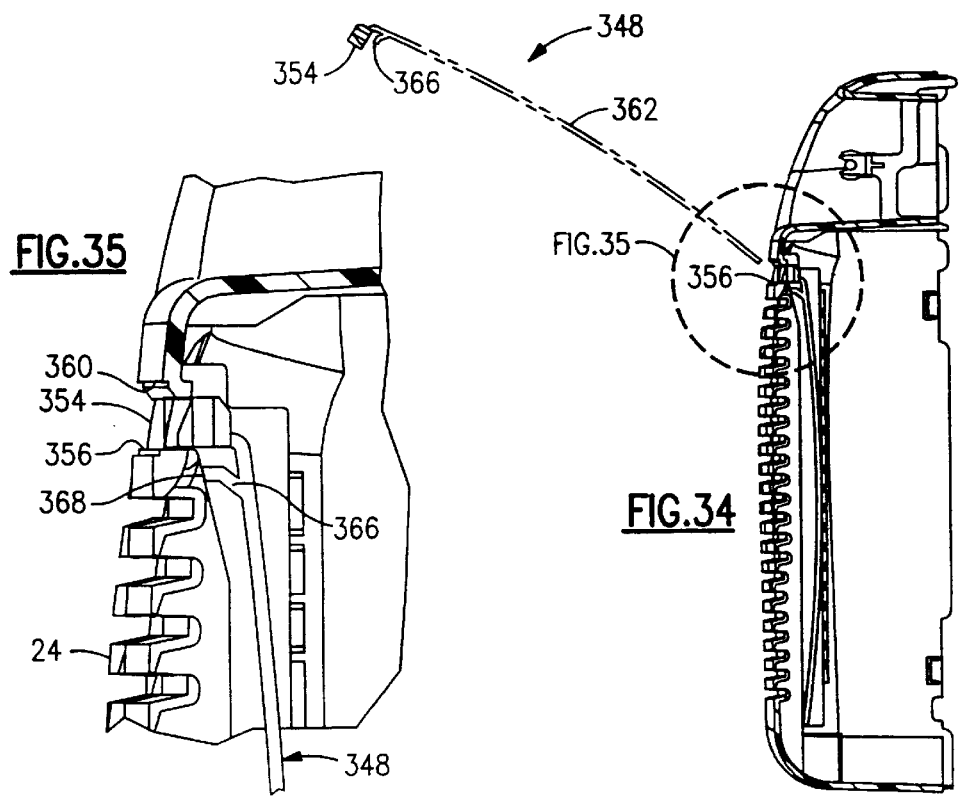
FIG.35
FIG.34

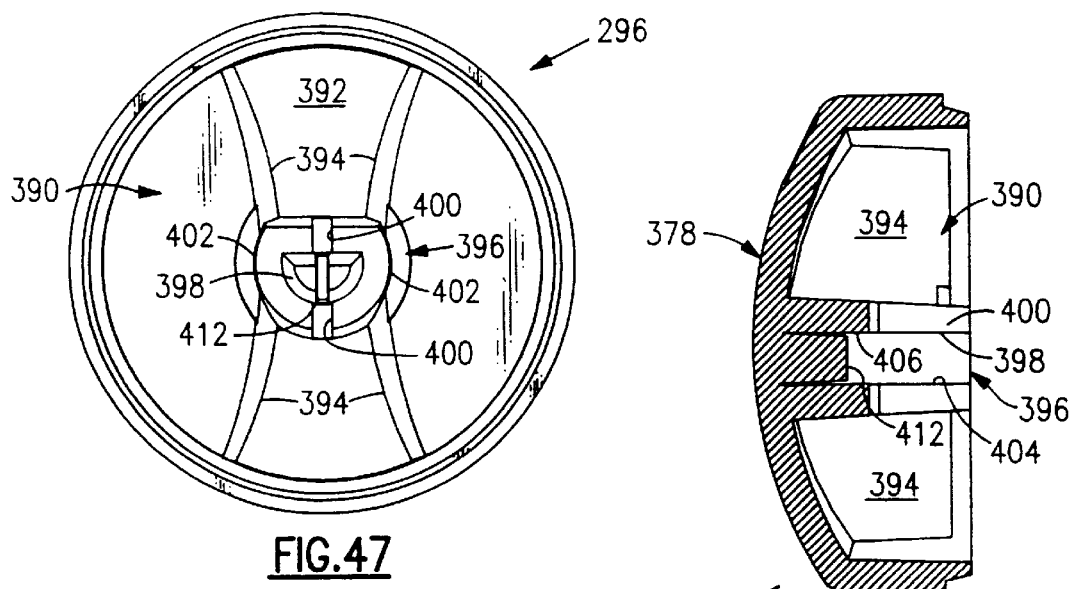
FIG. 47
FIG. 46
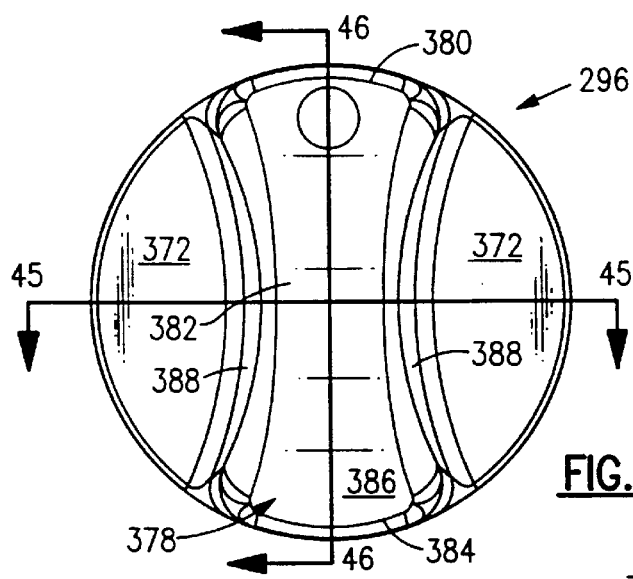
FIG. 44
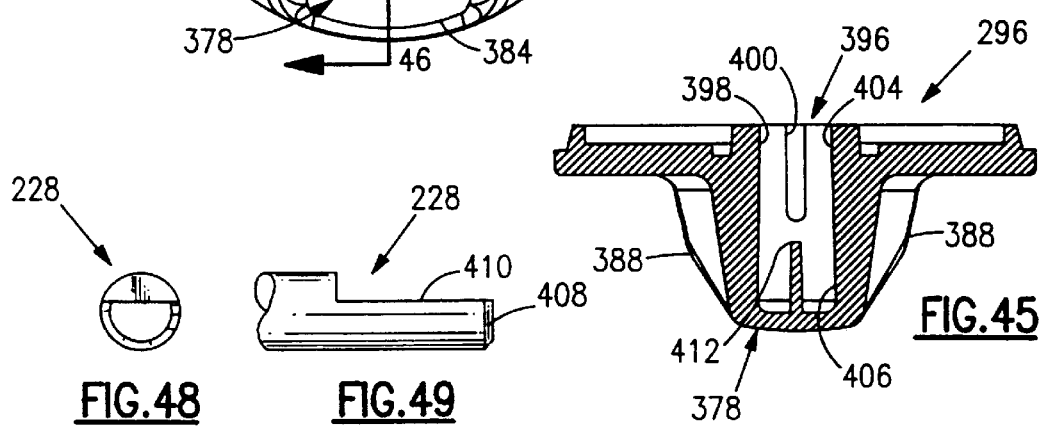
FIG. 48    FIG. 49    FIG. 45

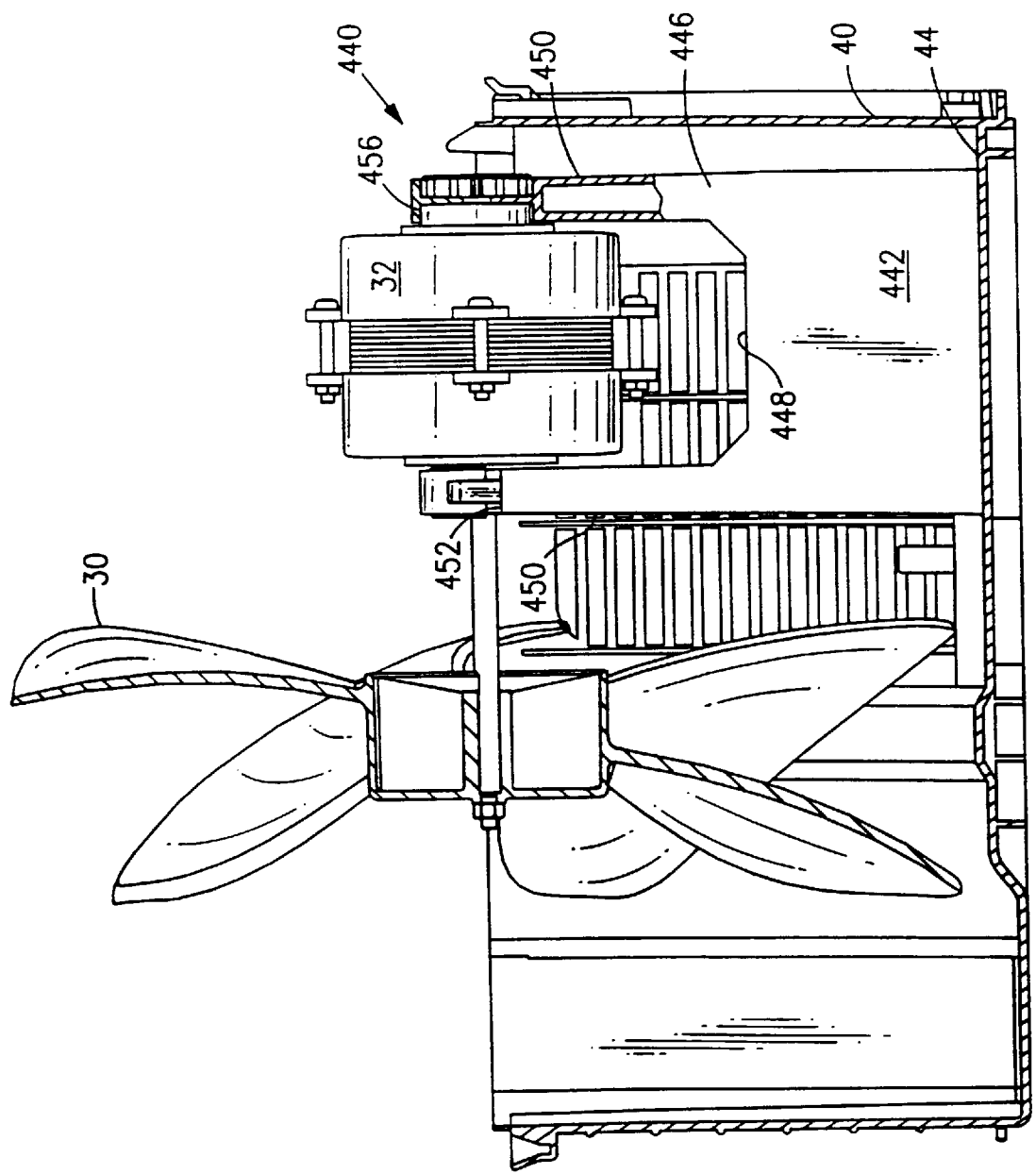

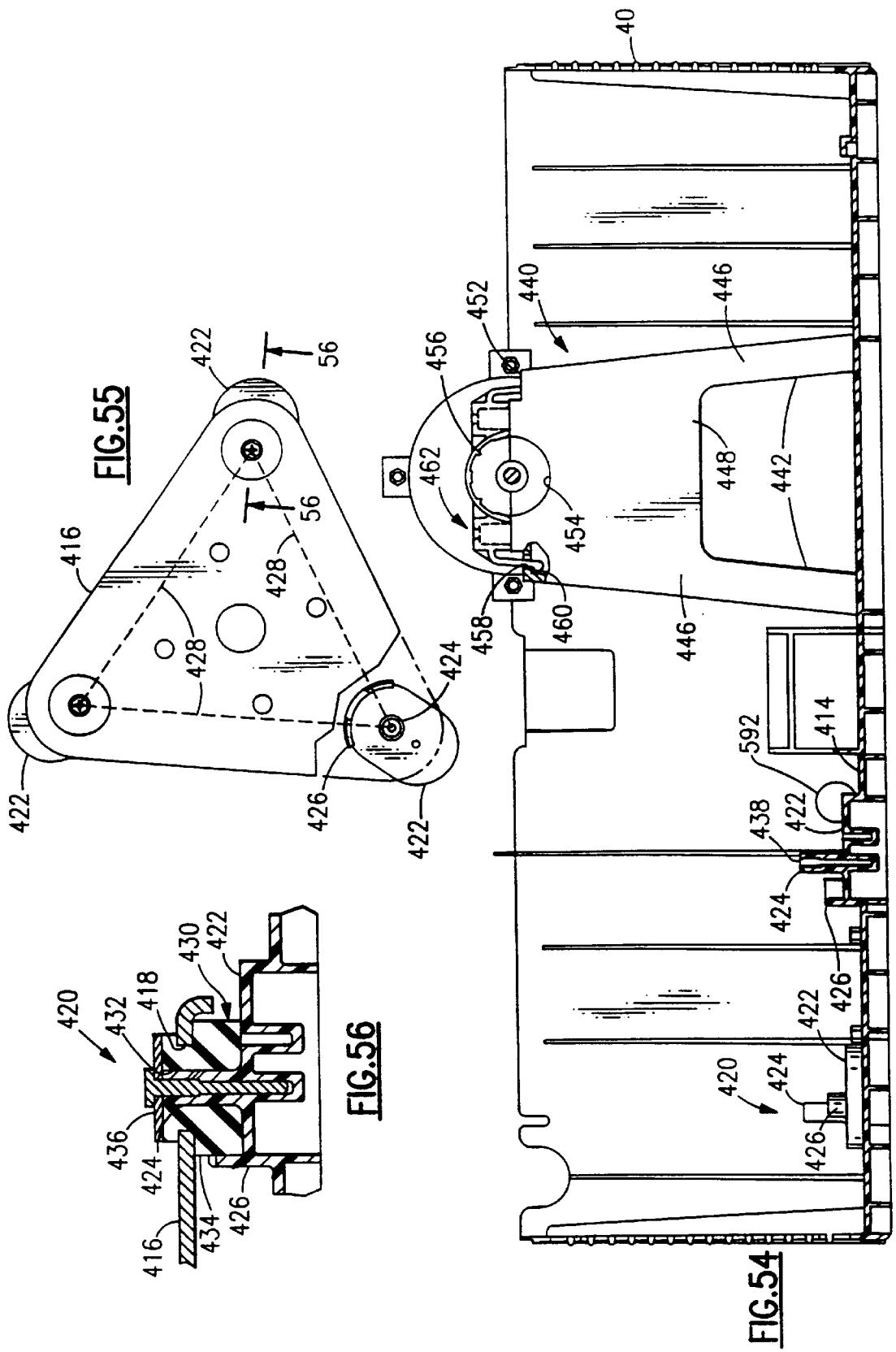

FAN AND MOTOR ASSEMBLY FOR AN AIR CONDITIONER

TECHNICAL FIELD

The present invention is directed to air conditioners, and more particularly to a subassembly of a fan and motor for use in the evaporator section of an air conditioner.

BACKGROUND ART

Room air conditioners generally comprise an inside fan or blower, which is powered by a motor to draw air through an evaporator coil to be cooled and to direct the cooled air back into the space being cooled. Such air conditioners also include a condenser coil for dissipating the heat picked up by the evaporator coil and a second fan is provided to cause an air flow over the condenser coil to increase the heat dissipation of that coil. A compressor is provided to increase the pressure of a refrigerant which is then supplied to the evaporator coil for evaporation and thus cooling.

Due to the complexity of and numbers of parts associated with a room air conditioner, assembly of such a device often times includes complicated and time intensive assembly steps and requires intricate manipulation of parts and tools. Such a process results in an increased cost of the room air conditioner due to increased manufacturing costs.

Whenever it is possible to assemble components of such an air conditioner in a manner requiring fewer fasteners or to occupy less space, it is considered desirable. It is considered particularly desirable in an air conditioner of the type having a separate motor and fan arrangement for the indoor or evaporator section for the assembly of such motor and fan to be as simple as possible and occupy as little axial space as possible.

DISCLOSURE OF THE INVENTION

According to the present invention, a subassembly of an electric motor and a fan for use in an air conditioner includes a centrifugal fan adapted for rotation about a longitudinal axis. The fan has an open inlet end at one longitudinal end thereof and convex closed end partition defining a cup-shaped space at the other axial end thereof. The fan motor comprises a housing having an axial length and a width and a drive shaft extending from one axial end thereof. The closed end partition of the centrifugal fan has a centrally disposed axially extending opening therethrough through which the drive shaft of the motor is adapted to be received and operatively attached. The width of the motor housing and the cup-shaped space are sized to allow a substantial portion of the axial length of the motor housing to be received within said cup-shaped space when the drive shaft is operably attached to the partition. In a preferred embodiment, an evaporator module for an air conditioner includes a structural indoor housing having a rear wall which is provided with an axial opening therein which is adapted to receive at least a portion of the evaporator fan motor therein. The rear wall further includes fan support structure associated therewith, which defines said opening. The fan support structure is adapted to extend into said cup-shaped space to engage the fan support structure to support the fan and motor subassembly in its desired operative position with respect to the housing.

BRIEF DESCRIPTION OF THE DRAWINGS

The invention may be better understood and its objects and advantages will become apparent to those skilled in the art by reference to the accompanying drawings, in which:

FIG. 10 is a perspective view of the air conditioner unit of FIG. 1 with a number of the internal component of the indoor module removed, and the outdoor module top housing removed therefrom;

FIG. 19 is a front elevational view of the indoor fan scroll;

FIG. 20 is a sectional view taken along the lines 20—20 of FIG. 19;

FIG. 21 is a sectional view taken along the lines 21—21 of FIG. 19;

FIG. 22 is a back elevational view of the indoor fan scroll;

FIG. 23 is a sectional view taken along the lines 23—23 of FIG. 22;

FIG. 24 is a front elevational view of the scroll enclosure;

FIG. 25 is a sectional view taken along the lines 25—25 of FIG. 24;

FIG. 26 is a sectional view taken along the lines 26—26 of FIG. 24;

FIG. 33 is a front elevational view of the indoor module front grille with the snap-in filter assembly in place;

FIG. 34 is a sectional view taken along the line 34—34 of FIG. 33;

FIG. 35 is an enlarged view of the area in FIG. 34 identified as FIG. 35;

FIG. 44 is a front view of a control knob;

FIG. 45 is a view taken along the lines 45—45 of FIG. 44;

FIG. 46 is a view taken along the lines 46—46 of FIG. 44;

FIG. 47 is a rear view of the control knob of FIG. 44;

FIG. 48 is an end view of a shaft to which the control knob is mounted;

FIG. 49 is a side view of the shaft of FIG. 48;

FIG. 53 is a view of the outdoor module taken along the lines 53—53 of FIG. 3;

FIG. 54 is a view of the outdoor module taken along the lines 54—54 of FIG. 3 with some of the internal components thereof removed;

FIG. 55 is an enlarged plan view of the compressor mounting structure illustrated in FIG. 54;

FIG. 56 is a view taken along the lines 56—56 of FIG. 55;

BEST MODE FOR CARRYING OUT THE INVENTION AND INDUSTRIAL APPLICABILITY

Figure 1:
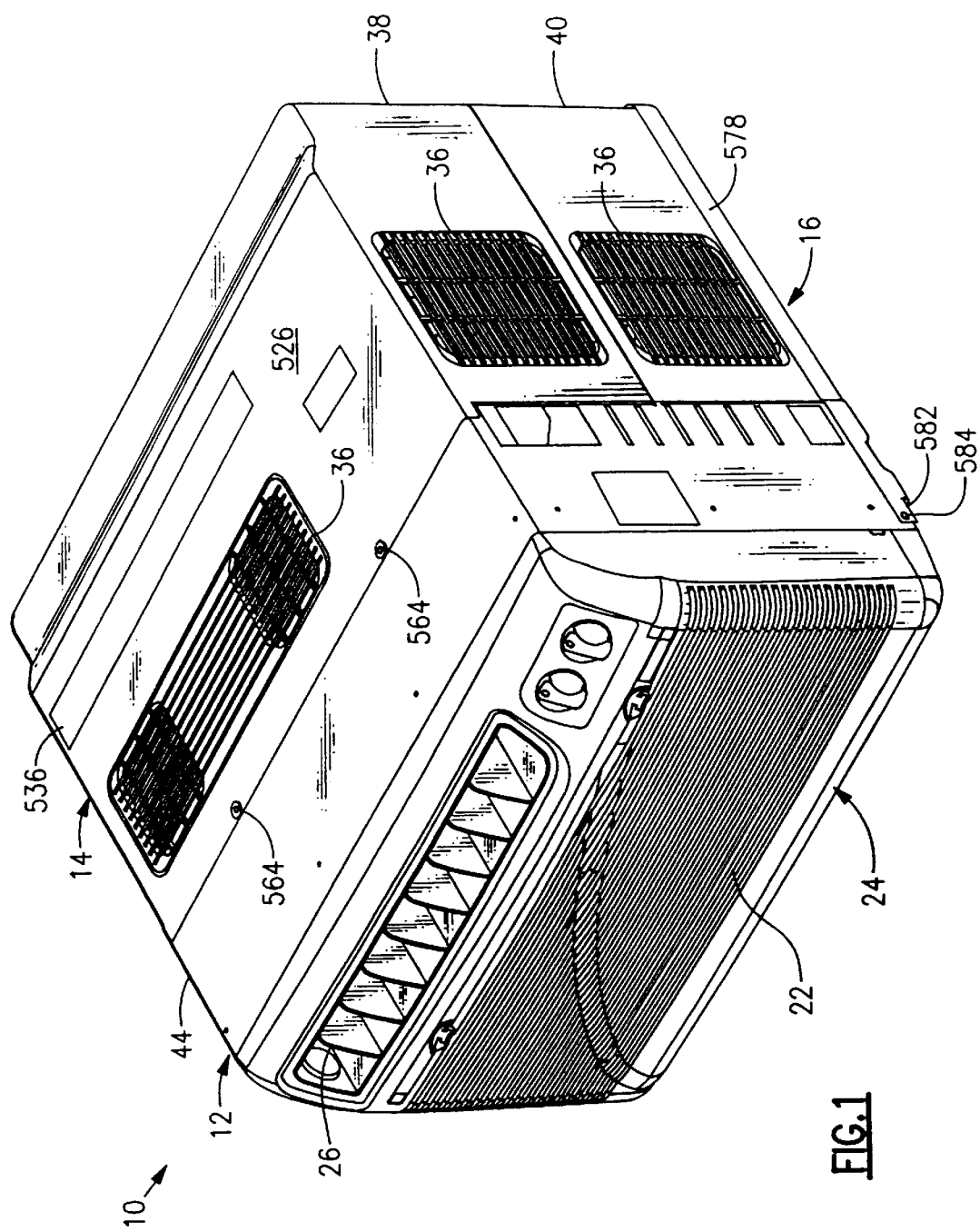
FIG. 1 is a perspective view of a room air conditioner which embodies the features of this invention.
Figure 65:
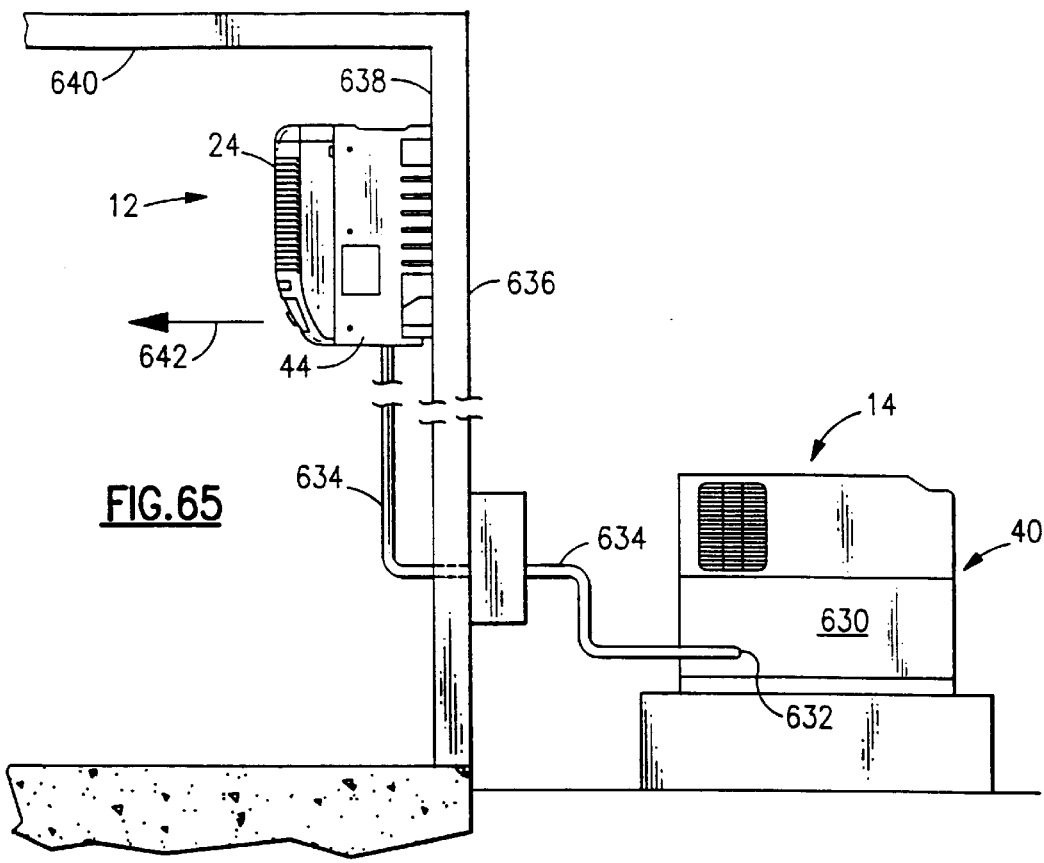
FIG. 65 is a schematic illustration of a typical installation of an air conditioner of the split system type according to the present invention.
Figure 66:
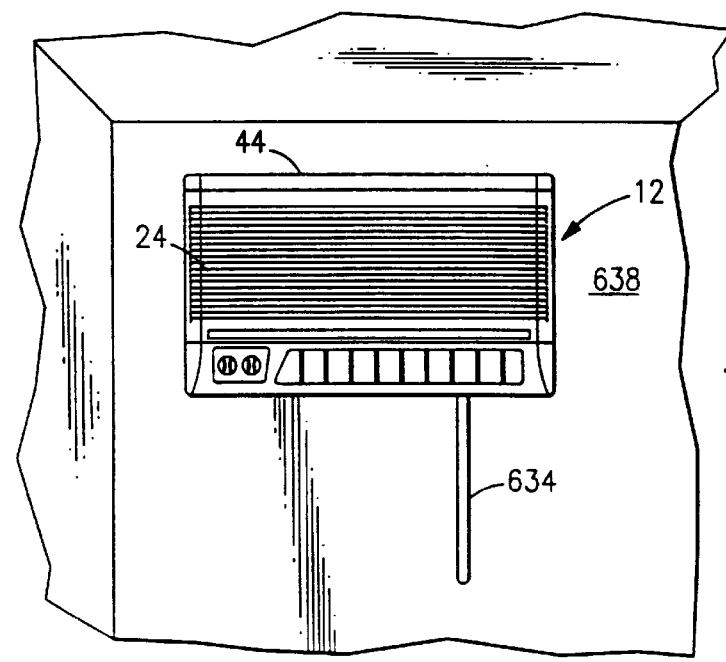
FIG. 66 is a front plan view of the indoor unit of FIG. 65.

With reference, initially, to FIG. 1, an air conditioning unit 10, according to the present invention, includes an indoor module 12 and an outdoor module 14 integrally attached to one another and mounted in a metal base pan 16 for use as a room air conditioner ("RAC"). It will be appreciated as the description of the invention proceeds that the indoor module 12 and the outdoor module 14 may be manufactured as independent modules, with some minor modification, for use as a split system air conditioner as illustrated in FIGS. 65 and 66 and will be described in more detail hereinbelow.

The RAC unit is adapted to be positioned in a rectangular opening in an exterior wall or on a window sill in a room where cooling is desired, with the indoor module 12 facing into the room as in conventional. The indoor module 12 comprises an indoor refrigerant to air heat exchanger 18 (hereinafter "evaporator coil") and an inside or evaporator fan 20. Air from the space to be conditioned by the system is drawn into the indoor module 12, by action of the evaporator fan 20, through inlet louvers 22 formed in an indoor grille 24 and is directed through the evaporator coil 18 where the air is cooled, before exiting from the indoor module 12 through an indoor conditioned air discharge assembly, generally 26.

The outdoor module 14 of the air conditioner unit is located outside of the space whose air is to be conditioned. The outdoor module contains, as best seen with reference to FIGS. 3, 10 and 50, an outdoor refrigerant to air heat exchanger or coil 28 (hereinafter "condenser coil 28"), an outdoor fan 30, an outdoor fan motor 32 and a compressor 34. In operation, ambient air enters the outdoor module 14 through a number of louvered air inlets 36 located in the upper 38 and lower 40 sections of the outdoor module housing. The air entering the outdoor module then passes through the outdoor fan 30 into the interior of the outdoor module from where it is forced through the condenser coil 28 before exiting from the outdoor section 14 through discharge louvers 42 in the back of the outdoor module.

Figure 2:
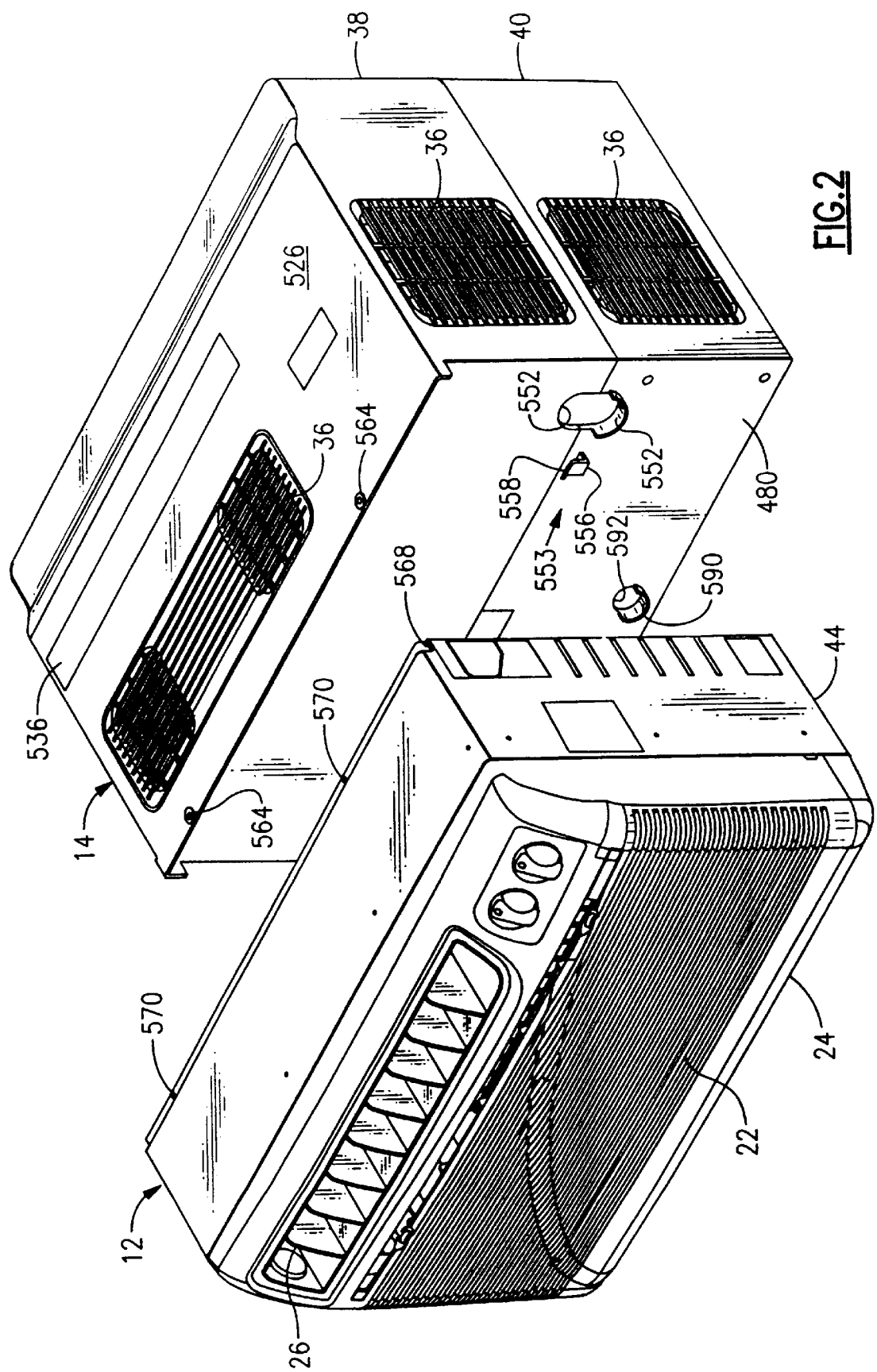
FIG. 2 is a perspective view of the air conditioner of FIG. 1 removed from the base pan and showing the separate indoor and outdoor modules.

FIG. 2 illustrates the indoor module 12 and the outdoor module 14 separated from one another. With reference to this FIG. 2 and FIGS. 3 through 26, construction of the indoor module will be described in detail. All of the components of the indoor module are assembled to the indoor housing 44, which is illustrated without any components assembled thereto in FIGS. 11, 12 and 13. The indoor housing is a one piece component molded from a polymer material, such as polypropylene. The housing 44 generally is a rectangular enclosure having a rear wall 46, top and bottom walls 48 and 50, respectively, and left and right hand side walls 52 and 54, respectively. The housing is provided with numerous integrally molded structural attachment points for the various components of the indoor module 12. Other integrally molded components serve as guide and support structure for other components. Each of these structures will be individually described as the structure, which it cooperates with for attachment or support, is described.

Figure 18:
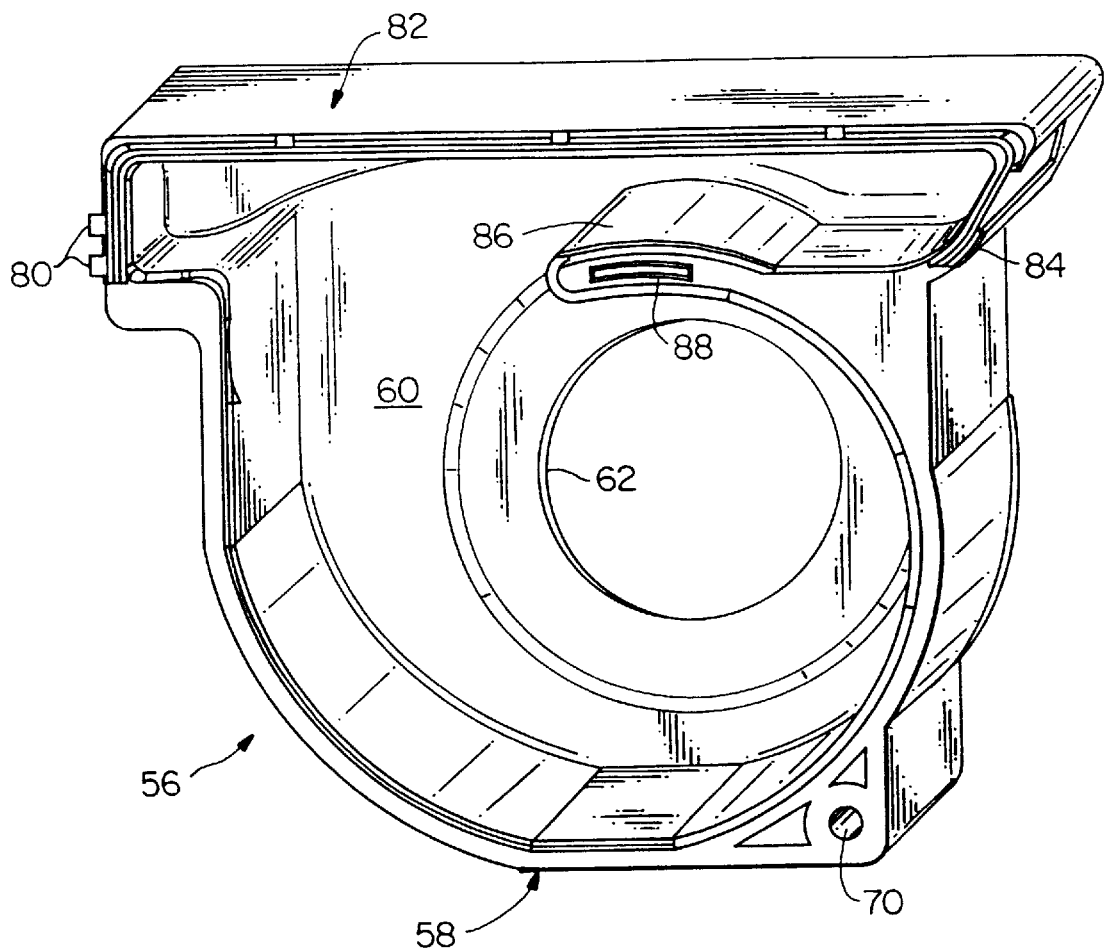
FIG. 18 is a perspective view of the indoor fan scroll.

The first component to be assembled to the indoor housing 44 is the indoor fan scroll 56 illustrated standing alone in FIG. 18 and in detail in FIGS. 19 through 23. The fan scroll is illustrated as installed in the indoor housing 44 in FIGS. 3, 4 and 6. The indoor fan scroll 56 is a single piece preferably molded from an expanded polystyrene foam. It includes a lower body section 58 which has an open front and a closed back wall 60, which includes an opening 62 therein. The opening 62 is adapted to receive a cylindrical wall 64 which extends forwardly from the rear wall 46 of the indoor housing and which is provided at its free end thereof with structure for supporting the motor 68 for the evaporator fan 20.

Figure 13:
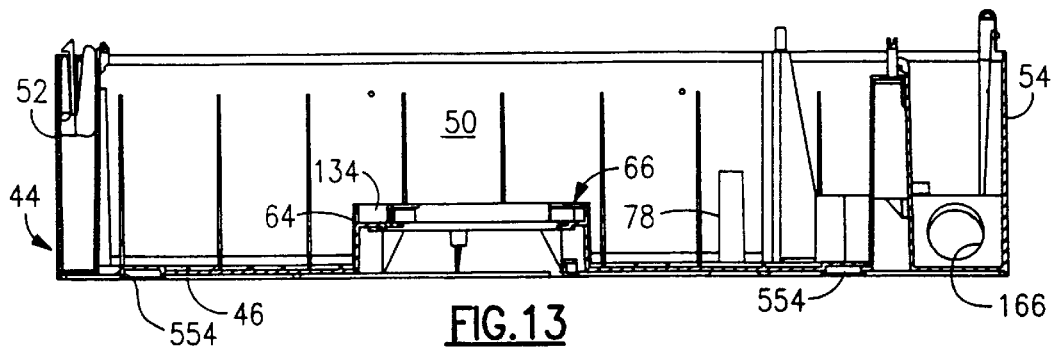
FIG. 13 is a sectional view taken along the lines 13—13 of FIG. 11.
Figure 11:
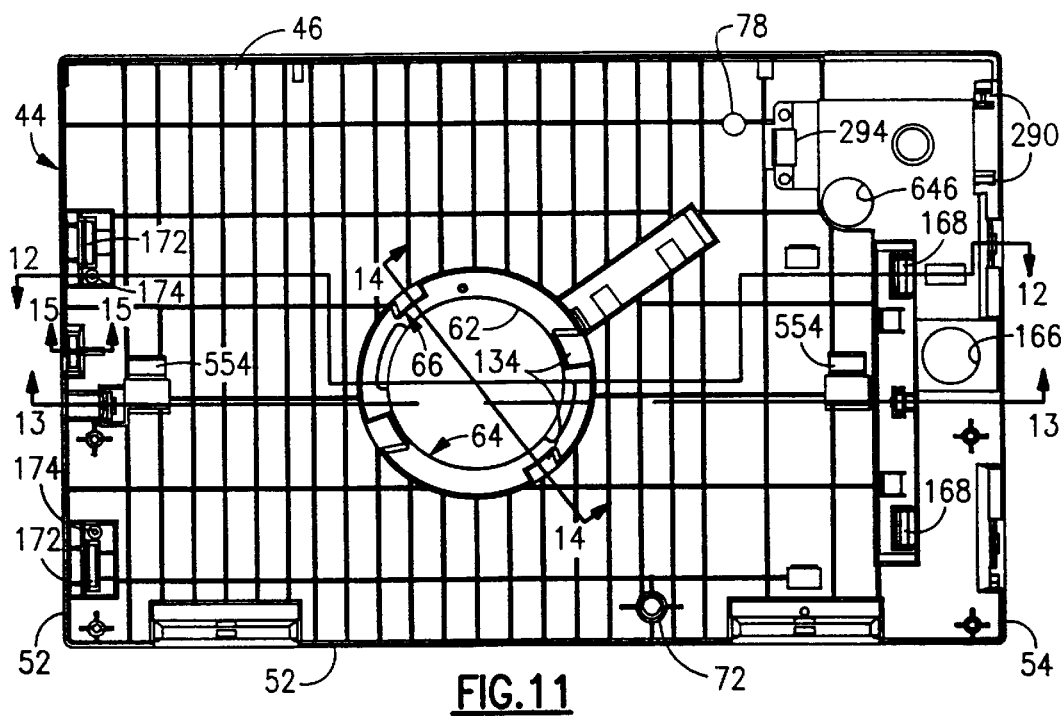
FIG. 11 is a front elevational view of the indoor module housing.
Figure 12:
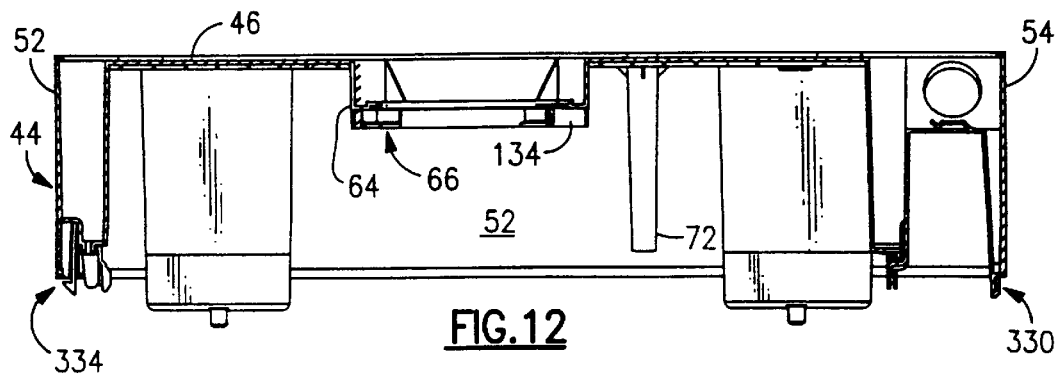
FIG. 12 is a sectional view taken along the lines 12—12 of FIG. 11.

The scroll 56 is provided with a through opening 70 at its lower right hand corner which is adapted to receive an elongated hollow tube 72 molded into the rear wall 46 of the indoor housing, as best seen in FIGS. 11 and 12. As will be appreciated, the tube 72 serves not only to locate the scroll, but is also an important part of the condensate disposal system of the air conditioner. A second positioning opening 74 is provided in the upper rear wall 76 of the scroll. This opening 74 is a blind opening and is adapted to receive a positioning pin 78 molded into the rear wall 46 of the indoor housing as best seen in FIG. 13. Accordingly, the scroll 56 is assembled to the indoor housing 44 by axially aligning the opening 60 in the back wall, the condensate drain tube 72 and the positioning pin 78 with their above described mating structure and simply sliding the scroll into its final position as illustrated in FIG. 6.

Additional scroll positioning surfaces, such as raised portions 80 on the left hand side of the upper section 82 of the scroll and surface 84 on the right hand side of the upper section, are adapted to engage fixed surfaces of the indoor housing to further facilitate positioning and support. It will be appreciated that the upper section 82 of the scroll communicates with the lower part 58 in which the indoor fan is mounted and, as illustrated clearly in FIG. 4, clearly serves as the air discharge plenum for conditioned air. With continued reference to FIG. 4 and FIGS. 18 and 20, an intermediate wall section 86 serves to further define and separate the lower part of the scroll 58 from the upper discharge section 82. This solid wall section contains an elongated arcuate opening 88 therein. This opening is engaged by mating structure provided on the back side of the upper end 92 of a scroll enclosure element 90, which will be described in detail hereinbelow.

Following installation of the scroll 56, a subassembly of the evaporator fan motor 68 and the evaporator fan 20 is assembled to the mounting structure 66 carried by the indoor fan support extension 64. Looking first at FIGS. 6 and 7, the indoor fan motor comprises a substantially cylindrical electric motor having a drive shaft 94 extending from one end thereof. The motor drive shaft has a flat 96 formed on one side thereof and a shoulder 98 from which extends a reduced diameter threaded end portion 100.

Figure 6:
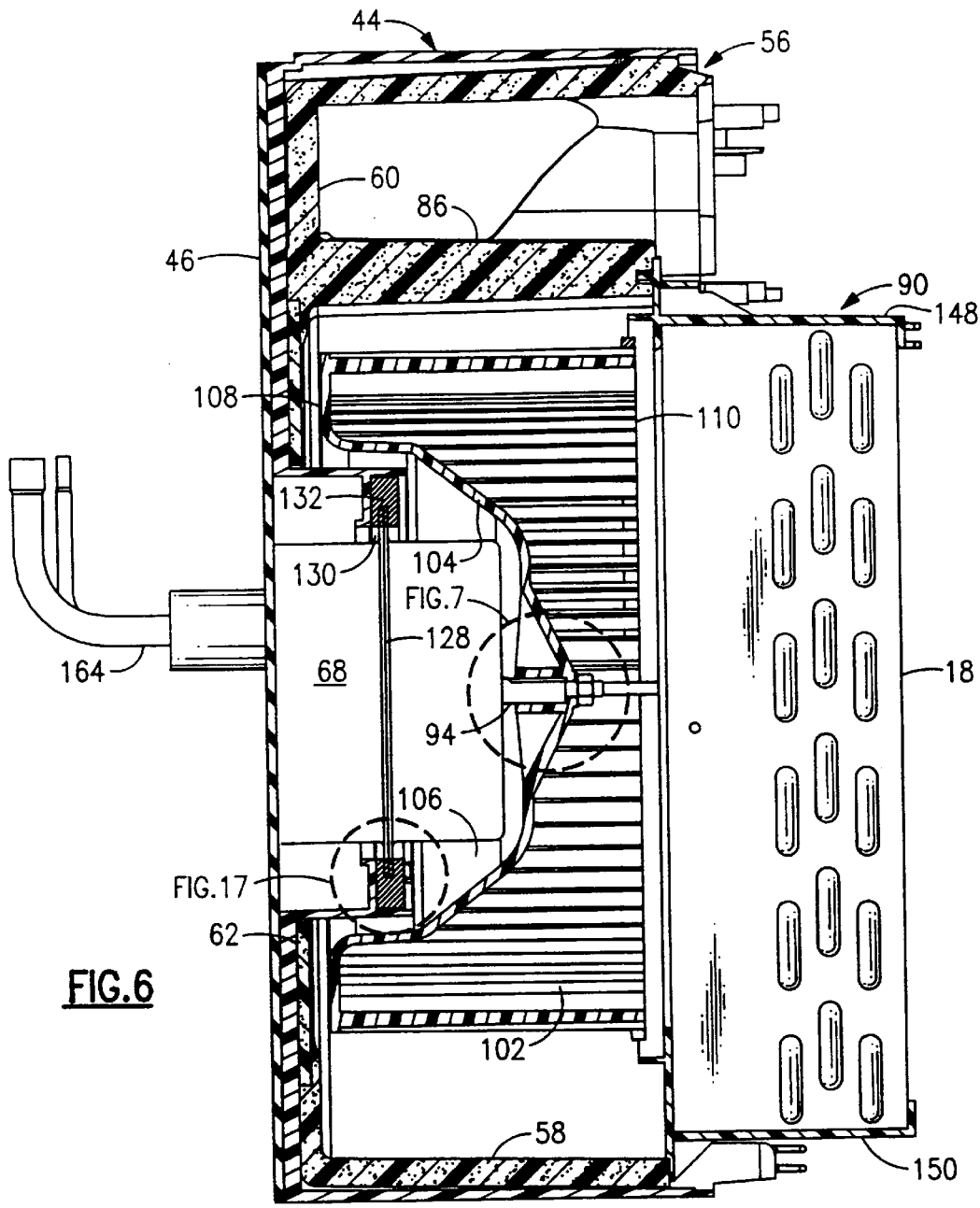
FIG. 6 is a left side view of the air conditioner as shown in FIG. 4 with some components shown in section and others broken away in order to show internal components thereof.

The evaporator fan 20, as best seen in FIG. 6, is a centrifugal fan having a plurality of longitudinally extending blades 102 positioned about the periphery thereof. The inlet of the fan is a large circular opening which is in air flow relationship with the evaporator coil 18. The back side of the fan is closed by a convex shaped partition 104, which defines a substantially cup-shaped space 106 in the back side of the fan. As best shown in FIG. 6, the partition 104 is defined by a number of linear extending sections to define the cup-shaped space 106 so that the space extends a substantial axial distance from the back 108 of the fan towards the inlet end 110 of the fan.

Figure 7:
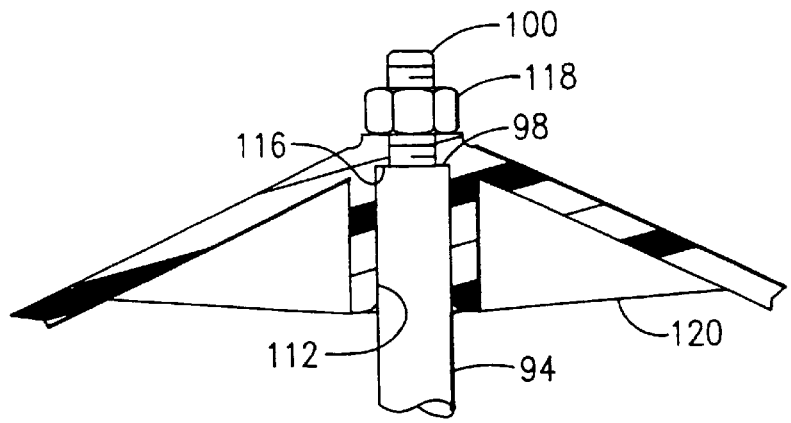
FIG. 7 is an enlarged view of the area in FIG. 6 identified as FIG. 7.

An axially extending opening 112 is provided at the center line of the fan through the partition wall 104. The opening 112 has a flat 114 formed thereon and is adapted to receive the motor drive shaft 94 and the flat 96 formed thereon with the shoulder 98 on the motor drive shaft engaging a mating shoulder 116 in the fan mounting opening 112. As illustrated in FIG. 7, the threaded extension 100 of the motor drive shaft 94 extends through the opening and receives a threaded nut 118 thereupon to attach the motor drive shaft 94 to the fan 20.

Figure 9:
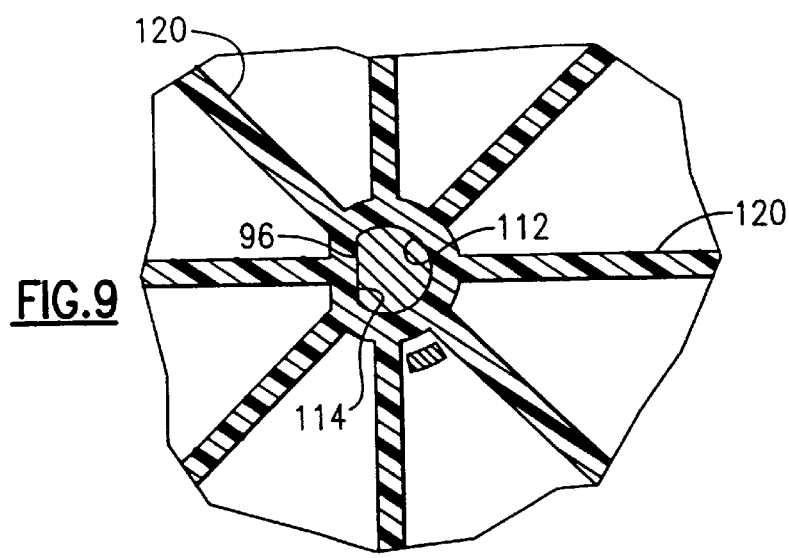
FIG. 9 is a sectional view taken along the lines 9—9 of FIG. 8.
Figure 8:
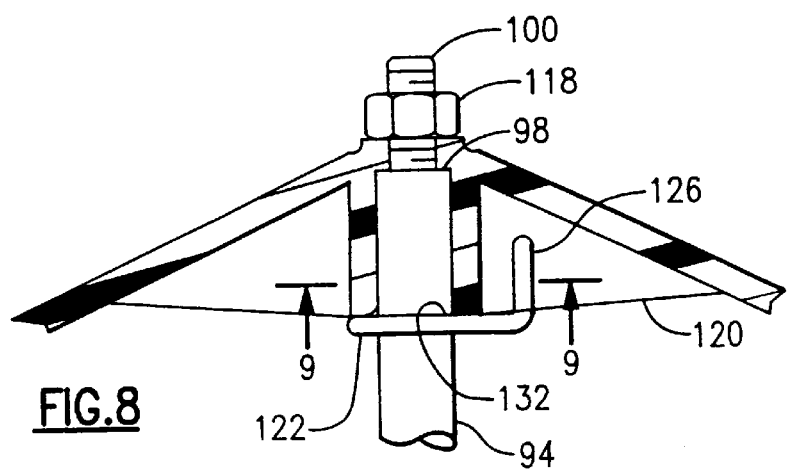
FIG. 8 is an alternative embodiment of the fan and motor attachment illustrated in FIG. 7.

As best seen in FIGS. 7, 8 and 9, a plurality of radially extending re-enforcing webs 120 extend from the structure defining the fan mounting opening 112 to the partition wall 104. FIGS. 8 and 9 illustrate an alternative embodiment to the fan/fan motor attachment. Reference number 122 is applied to a washer-like element, which has an opening 124 therethrough, having a cross section to receive the motor drive shaft 94 section with the flat 96 formed thereon. A leg 126 is provided on the washer 122 which is sized to extend between two adjacent re-enforcing ribs 120 as illustrated in FIG. 9. This arrangement assures a positive driving arrangement between the motor drive shaft 94 and the evaporator fan 20.

With continued reference to FIG. 6, it will be noted that as attached, the axial length and the width of the housing of the evaporator fan motor 68 and the axial and radial dimensions of the cup-shaped space 106 are such that when the motor is mounted to the evaporator fan as described, a substantial portion of the axial length of the motor housing is received within the cup-shaped space to thereby result in a minimal axial length of the subassembly of the evaporator motor 68 and the evaporator fan 20. This is achieved by contouring the fan partition 104 such that it defines the motor receiving cup-shaped space 106 while not substantially impairing the air flow of the centrifugal evaporator fan from the inlet and outwardly through the fan blades 102. As illustrated, more than seventy-five percent (75%) of the axial length of the housing of the evaporator fan motor 68 is received within the cup-shaped space 106.

Figure 16:
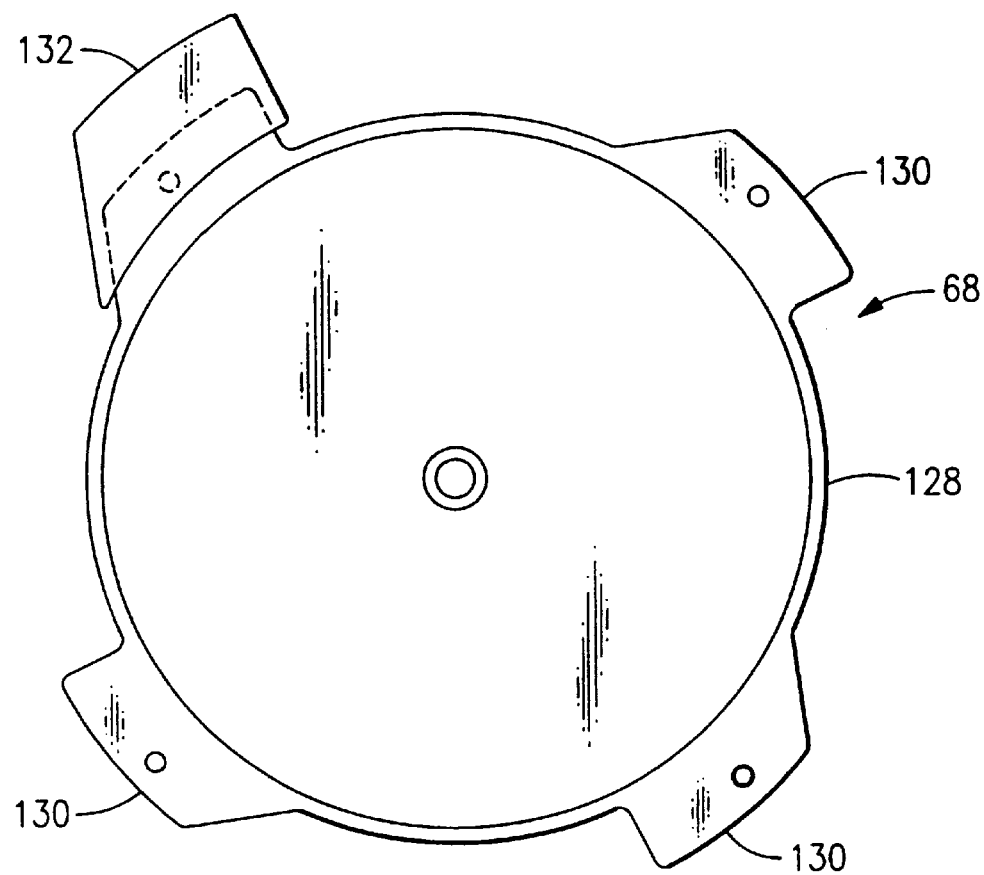
FIG. 16 is a simplified end view of the indoor fan motor and its associated mounting structure.

Looking now at FIGS. 6, 11 through 14, 16 and 17, the mounting of the evaporator fan 20/evaporator fan motor 68 subassembly to the indoor fan mounting structure 66 previously described is illustrated. Looking, first, at FIG. 16, a simplified end view of the housing 68 of an evaporator fan motor is shown to include a peripherally extending flange 128, which has four radially outwardly extending lugs 130 equally spaced thereabout. The flange 128 and the lugs 130 carried thereby are formed from a structural material and each of the lugs is provided with an outer cover or sleeve 132. The lug covers 132 are preferably made from an elastomeric material and are of substantial thickness relative to the thickness of the lug as illustrated in detail in FIG. 17. In a preferred embodiment, the lug covers 132 are made from a continuous formed rubber component, a part of which is shown in FIG. 16. The formed rubber component would be formed in a single piece, which may extend about the periphery of the motor and engage each of the flanges 128.

Figure 14:
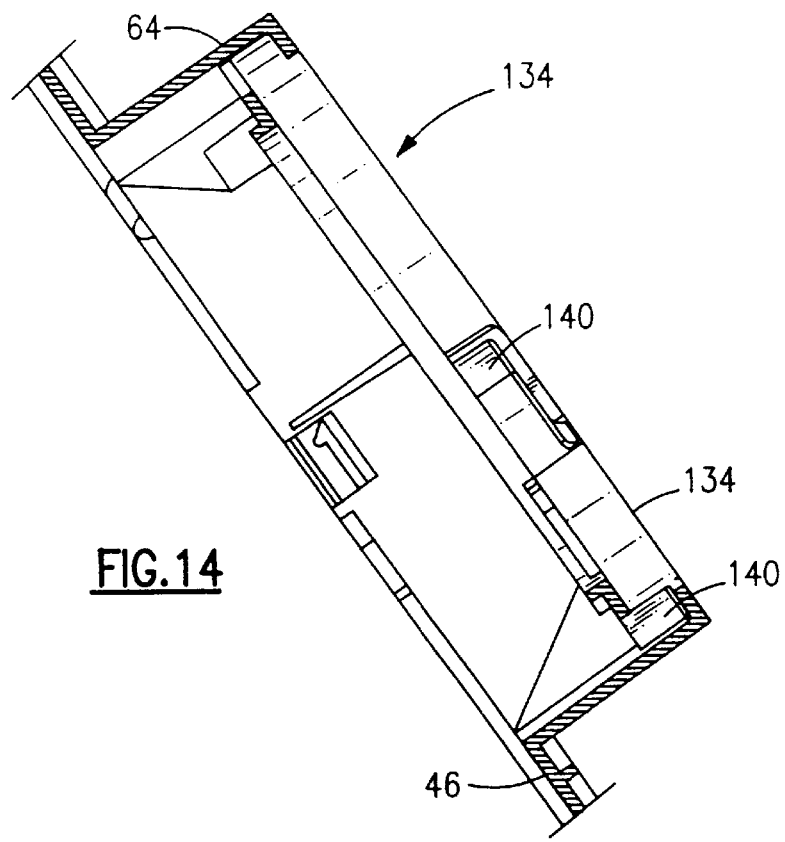
FIG. 14 is a sectional view taken along the lines 14–14 of FIG. 11.
Figure 17:
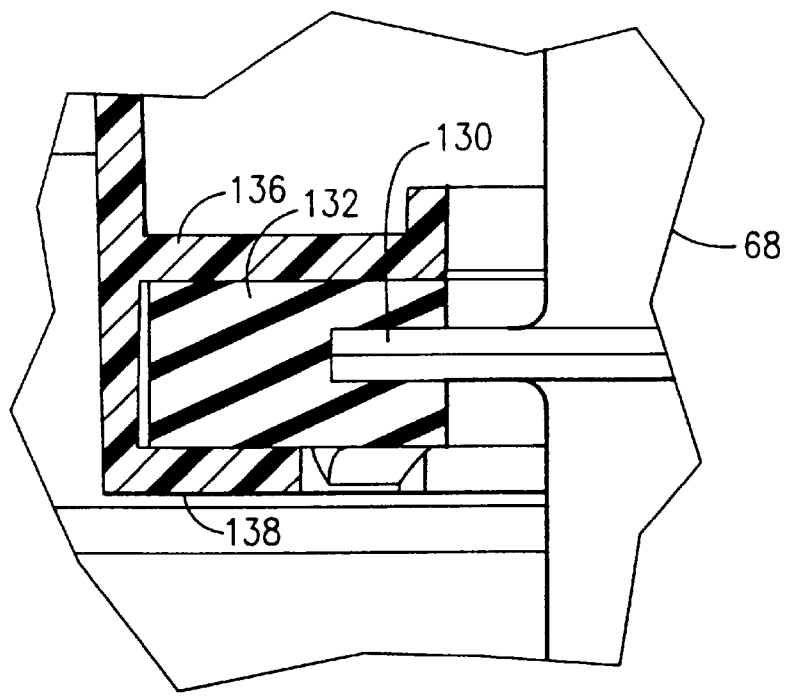
FIG. 17 is an enlarged partial view of the indoor fan motor mounting as shown in FIG. 16.

With the elastomeric covers 132 in place, the housing of the evaporator fan motor 68 is passed through the opening defined by the indoor fan support extension 64 with the four lugs 130 in alignment with receiving openings 134 formed in the mounting structure 66. The lugs 130 pass into the openings 134 to engage a rear wall 136. At this point the motor fan assembly is rotated counter-clockwise such that the lugs 130 and the covers thereon 132 are displaced under an outer wall 138 as best seen in FIG. 17. Continued rotation of the assembly results in the outer cover 132 of the lugs 130 engaging a stop wall 140 as best shown in FIG. 14. The engagement of the lugs 130 and lug covers 132 with the structure defined by the back wall 136, outer wall 138 and the stop walls 140 results in positive operative retention of the evaporator motor in the desired position without the need for any additional fasteners. It should be appreciated that the thickness of the elastomeric lug covers 132 results in a sound and vibration isolating mounting for the motors as well as serving as a part of the mounting structure.

Following assembly of the evaporator fan/motor subassembly to the housing 44 a subassembly of the previously mentioned scroll enclosure 90 and the evaporator coil 18 is assembled and installed to the indoor housing 44. The scroll enclosure 90 is shown in detail in FIGS. 24 through 26 and includes a substantially planar wall section 142 having a large circular opening 144 formed therein. The opening 144, is defined, as best seen in FIG. 26, with a rearwardly extending annular wall portion 146, which is adapted to receive the front or inlet end 110 of the evaporator fan therein when installed to the housing 44 to thereby define the inlet flow path from the evaporator coil 18 to the inlet of the fan.

Figure 4:
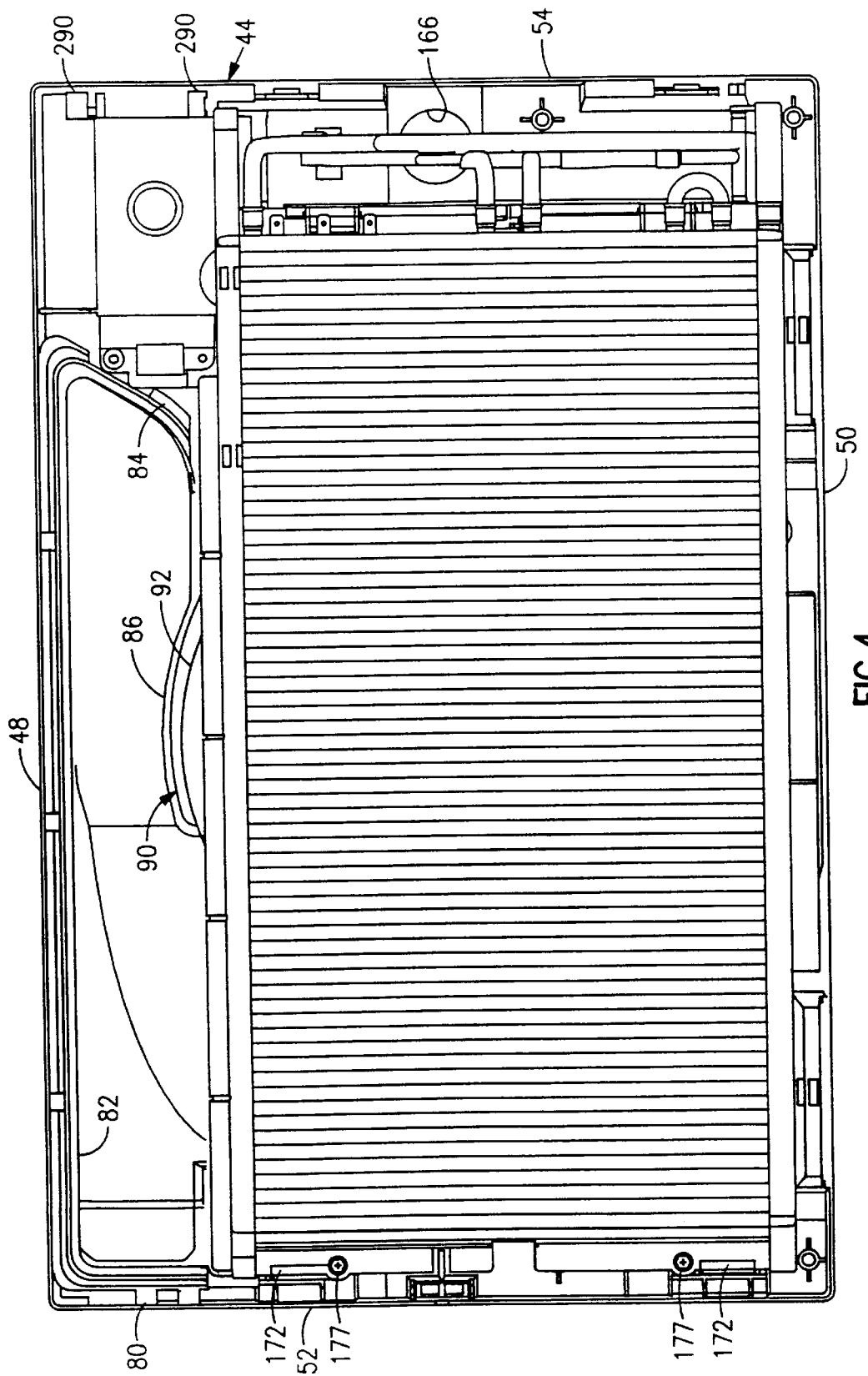
FIG. 4 is a front elevational view of the air conditioner of FIG. 1 with the front grille removed.

The scroll is provided with rectangularly shaped forwardly extending extensions 148 and 150 at the upper and lower ends thereof, respectively. The extensions 148 and 150 are provided with outer perimeter wall extensions 152 and 154 at the edges thereof, extending upwardly and downwardly, respectively. With reference to FIG. 6, these extensions and their associated perimeter wall sections are adapted to receive and retain the evaporator coil therebetween. Specifically, the spacing between the upper extension 148 and the lower extension 150 and their associated walls 152 and 154, respectively, are such that these sections must be flexed upwardly and downwardly respectively in order to receive the evaporator coil in the installed position as illustrated in FIG. 6. With reference to FIGS. 4 and 24, the scroll enclosure 90 includes a vertically extending left hand wall 156 and a vertically extending right hand wall 158, which are adapted to engage the left and right hand ends 160 and 162 of the evaporator coil to further retain the evaporator coil within the scroll enclosure 90.

Figure 3:
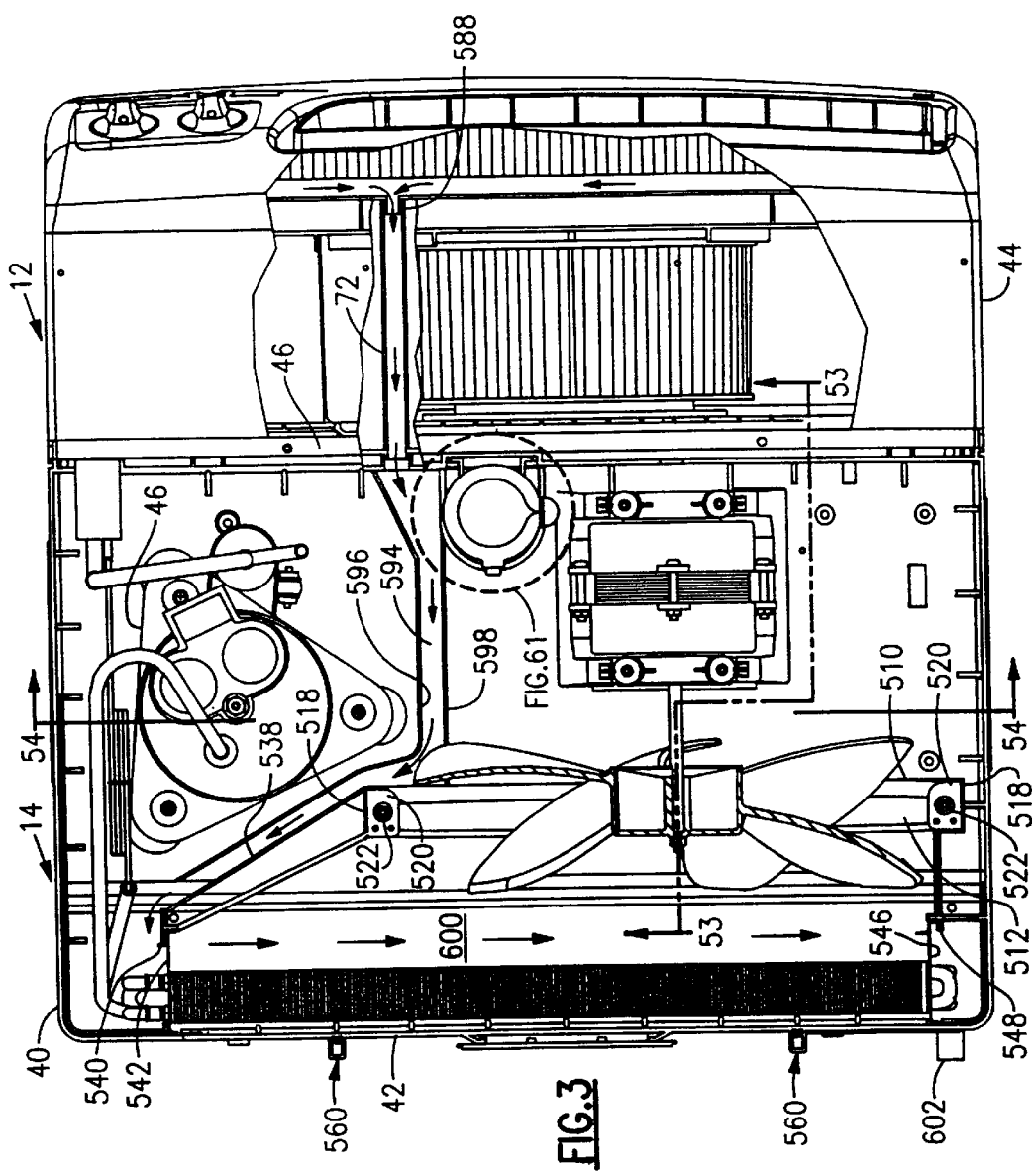
FIG. 3 is a top elevational view of the air conditioner of FIG. 1 with the cover of the outdoor module removed and the top of the indoor module partially broken away.
Figure 5:
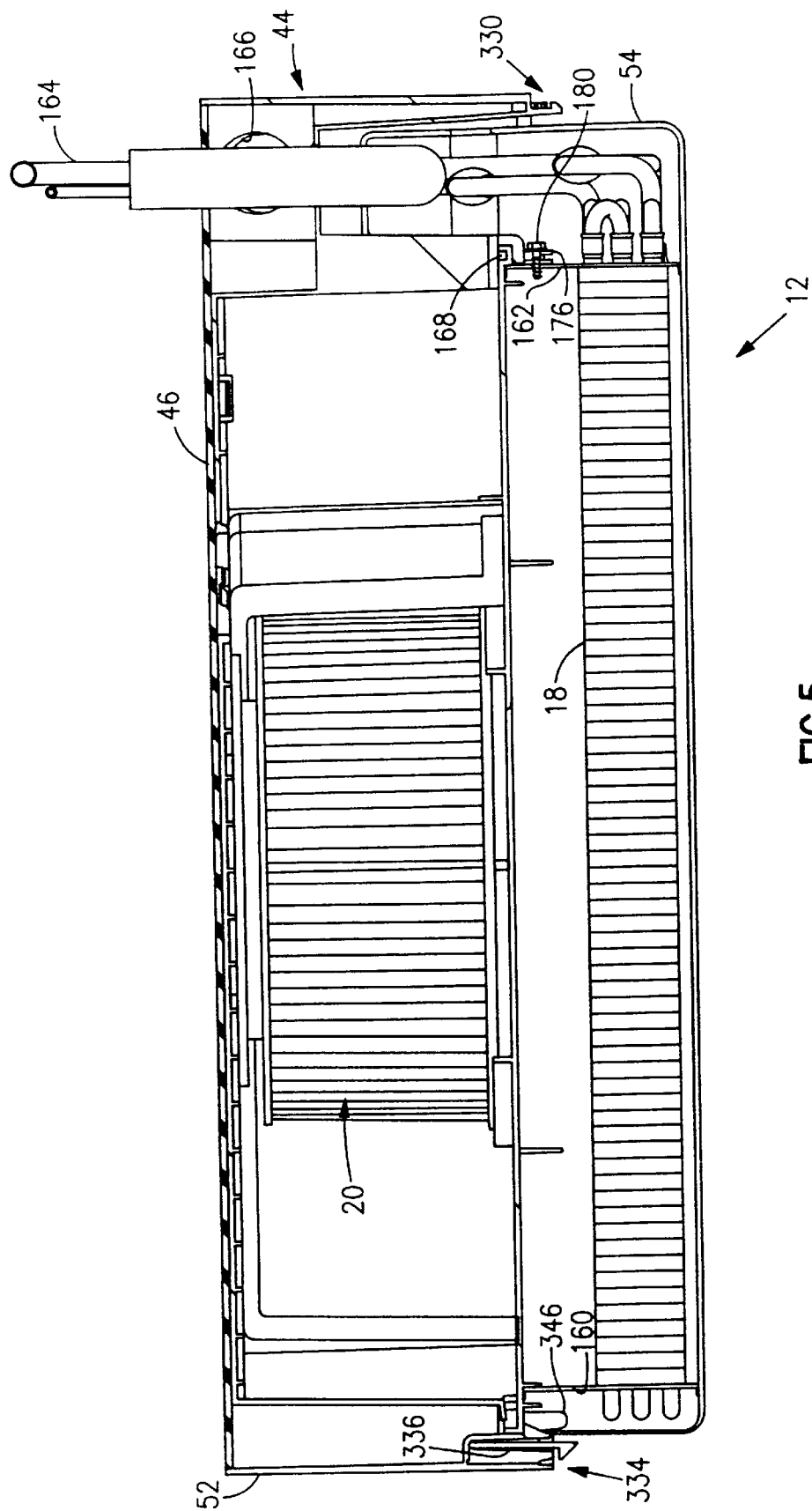
FIG. 5 is a top plan view of the indoor module with portions thereof broken away to show internal components thereof.

It should be understood that the subassembly of the scroll enclosure 90 and the evaporator coil 18 has several refrigerant tubes and capillaries extending therefrom generally identified by reference numeral 164 in FIGS. 3, 4 and 5. The free end of these tubes are passed through an opening 166 provided in the rear wall 46 of the indoor housing 44.

Following passage of the tubes 164 through the opening 166, assembly of the scroll enclosure/evaporator coil assembly is accomplished by engaging the vertically extending right hand wall 158 of the scroll enclosure with a pair of L-shaped hooks 168. Following such engagement, the left hand side of the assembly is rotated toward the indoor housing 44 such that an outside vertically extending wall 170 on the scroll enclosure is received by a pair of flexible latches 172 illustrated in FIGS. 4, 10 and 11 to thereby structurally retain the scroll enclosure and evaporator coil in its desired operative position.

As a back up or optional attachment arrangement, openings 174 are provided in the indoor housing 44 adjacent each of the flexible latches 172. These openings are adapted to be in axial alignment with a pair of openings 176 in the left hand wall 170 of the scroll enclosure 90 as illustrated in FIG. 24. Threaded fasteners 177, as illustrated in FIG. 4, may be used in the event that the flexible plastic latches 172, for example, become broken during servicing. An optional screw attachment arrangement is provided on the right side of the scroll housing also. This is best seen with reference to FIGS. 5 and 11, where it is seen that an extension 176 from the indoor housing 44 extends into confronting engagement with the right hand tube sheet 178 of the evaporator coil. A threaded fastener 180 is illustrated passing through the extension into an opening provided in the evaporator coil.

Turning now to FIGS. 39 through 43, the control box 182 which serves to house the units control switch 184, the thermostat 186 and the evaporator motor capacitor 188 is shown in detail. As will be appreciated, the control box 182 is made up from two molded plastic components, which are adapted to snap together and snap-fit into the upper right hand corner of the indoor housing 44.

The front section 190 of the control box includes a substantially planar front wall 192, which is provided with a pair of through openings for receiving the control shafts of the control switch 184 and the thermostat 186 therethrough. The switch 184 and the thermostat 186 are attached to suitable molded plastic mounting structure on the inside 196 of the front wall 192.

Extending rearwardly from the front wall 192 is a top wall 198, a bottom wall 200, a left side wall 202, and a right side 204, which cooperate to define a rearwardly facing skirt element on the front section 190. The top wall 198 is provided with a pair of forwardly facing hook-shaped elements 206. The bottom wall 200 is provided with a ramp-like recess therein 208 having a laterally extending protrusion 208 extending thereacross. The recess 208 tapers from the back edge 210 of the bottom wall outwardly to define a forward facing retaining surface 212.

Figure 40:
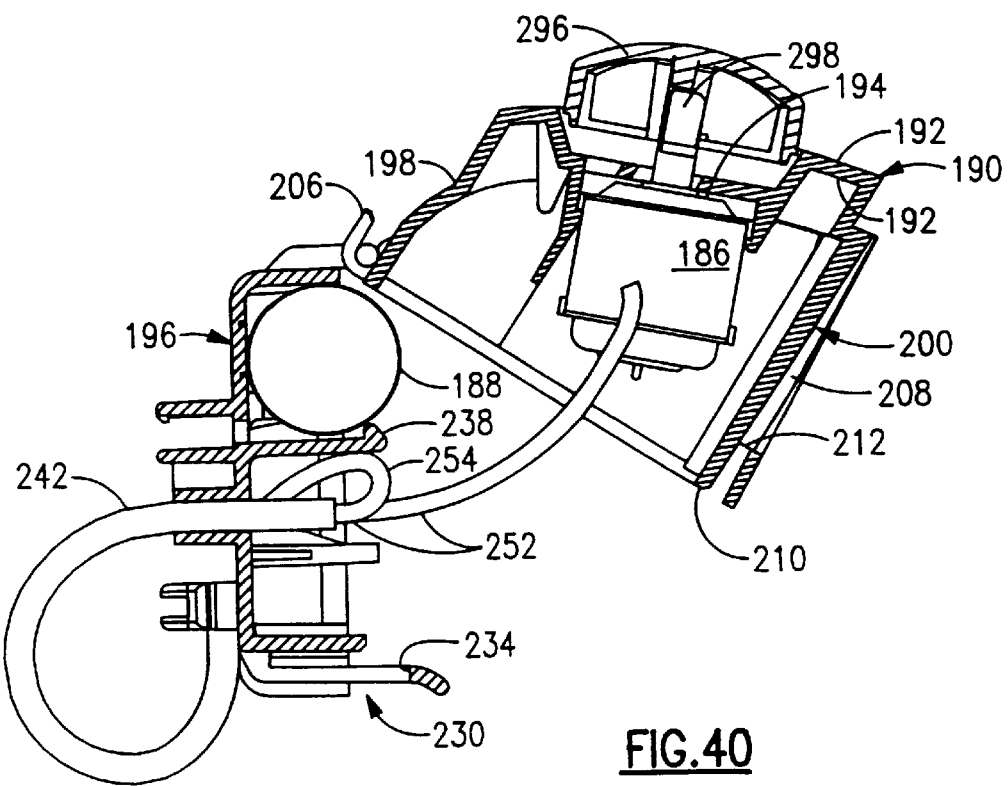
FIG. 40 is a side sectional view of the control box prior to closing.
Figure 41:
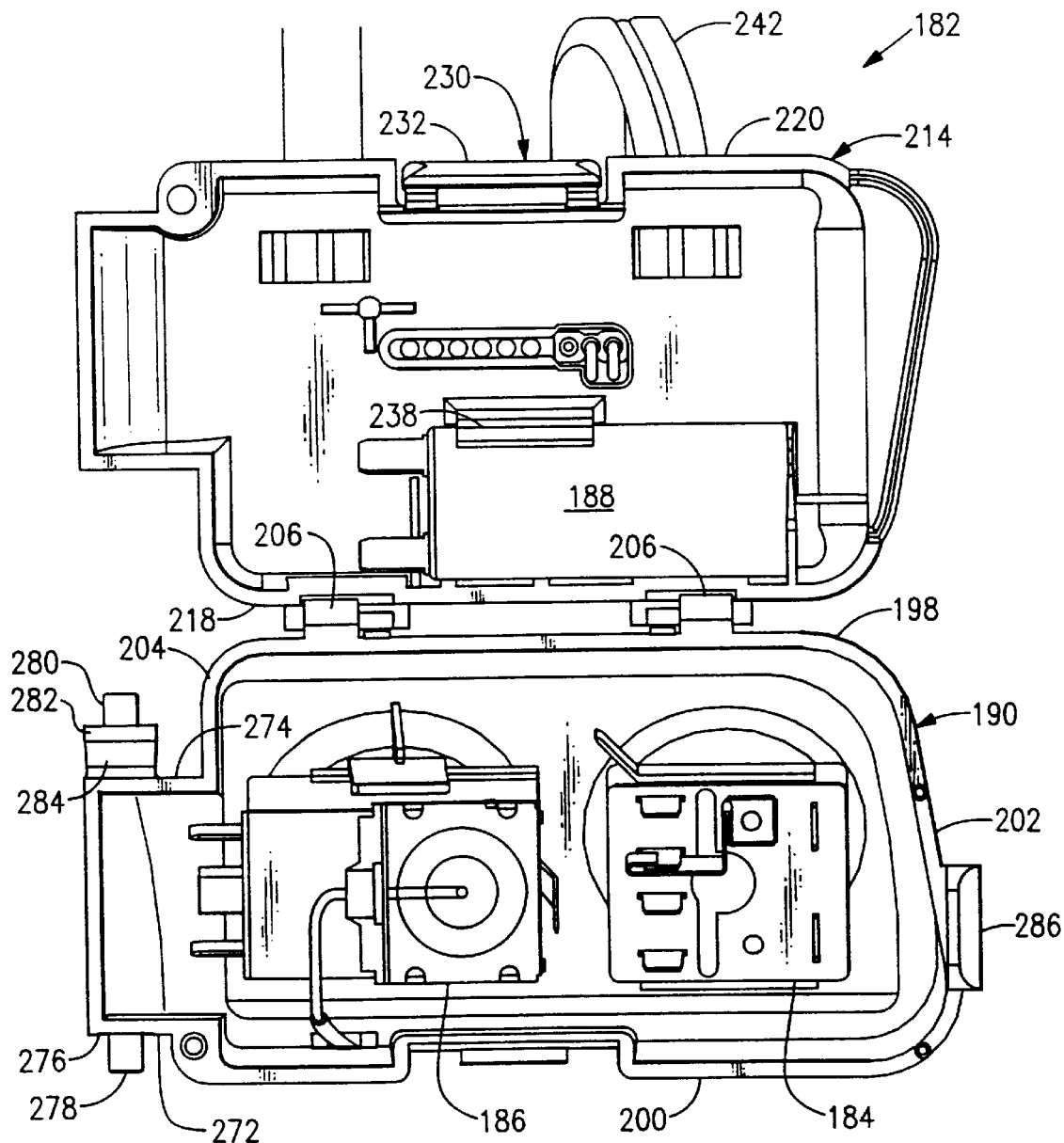
FIG. 41 is a sectional view of the two halves of the control box, partially assembled and open.
Figure 42:
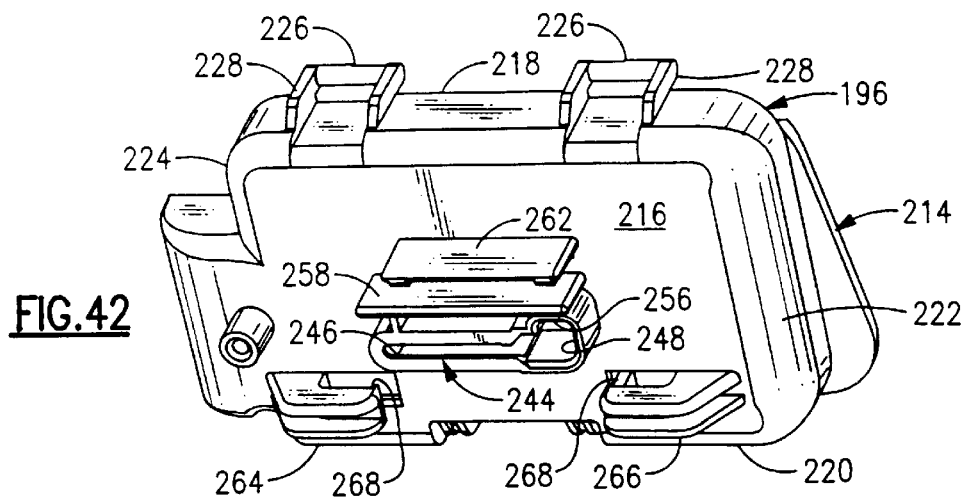
FIG. 42 is a rear perspective view of the back section of the control box.

The back section 214 of the control box also includes a substantially planar back wall 216 a top wall 218, a bottom wall 220, and left and right side walls 222 and 224, respectively, to define a forwardly facing skirt element. The forward edge of the top wall 218 is provided a pair of free standing laterally extending substantially cylindrical elements 226 adapted to operatively pivotally engage the hooks 206 provided on the front section 190. The transversely extending elements 226 are each supported by a pair of parallel support elements 228 integrally molded into the top 218 of the back section 214, as best shown in FIG. 42. As best shown in FIGS. 40 and 41, the bottom wall 220 of the back section is provided with a rearwardly extending flexible latching mechanism 230. The latch includes a transversely extending section 232 which defines a rearwardly facing surface 234 adapted to engage the forward facing surface 212 carried by the bottom wall of the front section 190.

Figure 43:
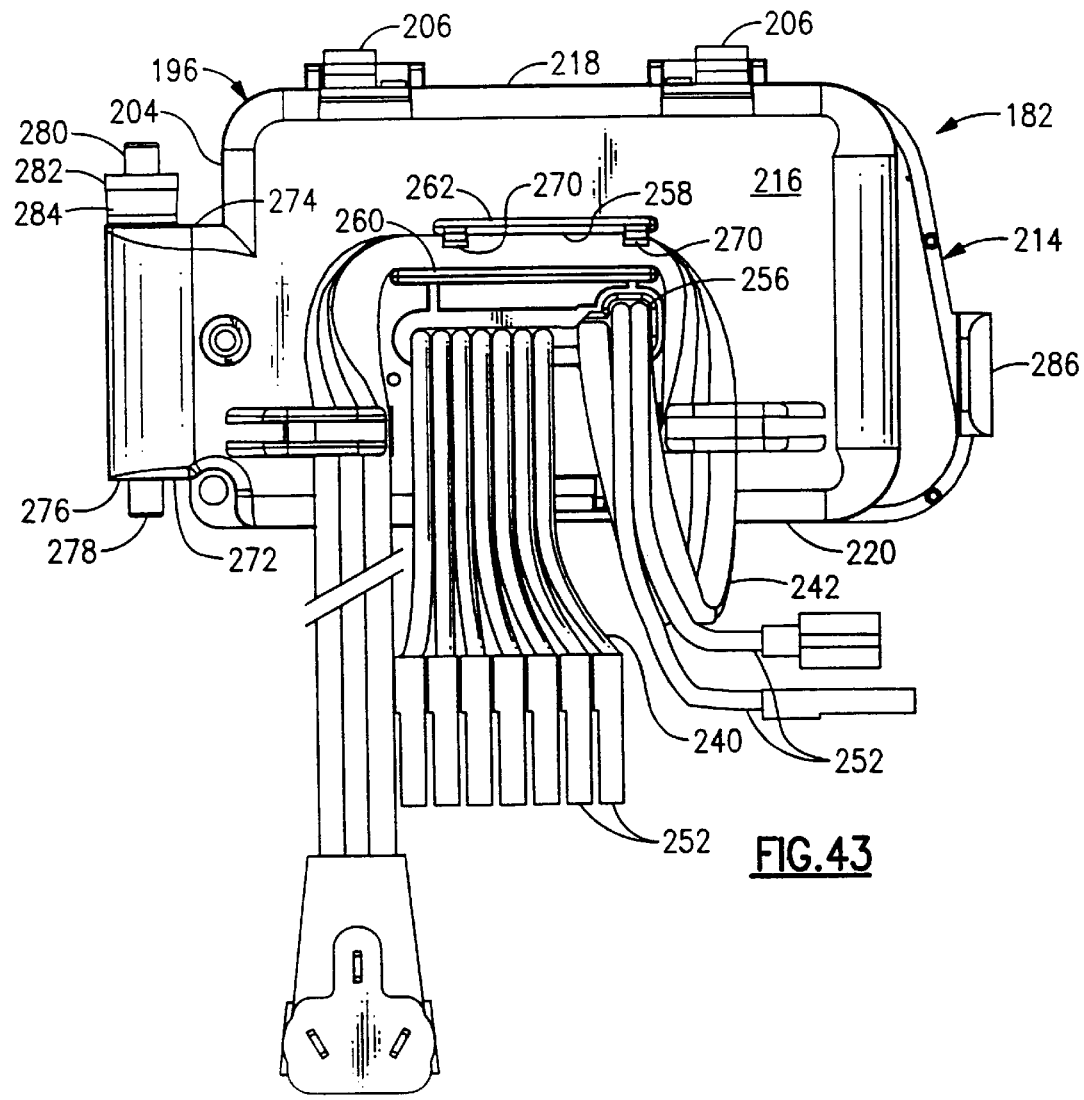
FIG. 43 is a back view of a fully assembled control box.

With reference now to FIGS. 40 and 41, a cylindrical plastic evaporator fan motor capacitor 236 is snap mounted by engagement with the inside of the top wall and a flexible latch 238 within the interior of the back section 214. While not all of the interior connections are shown, it should be appreciated that a number of individual electrical wires generally, 240, and an electrical service supply line 242 must extend into the interior of the control box 182. With reference to FIGS. 42 and 43, a single horizontally extending opening 244 is provided in the back wall 216 of the back section 214 for all of the wires 240 and 242 to pass. The opening 244 includes a narrow elongated section 246 in which a plurality of the smaller wires 240 may be sequentially arranged and supported. An enlarged section 248 is provided at one end of the opening 244 to receive the service power cord 242.

It will be noted that both ends of most of the wires 240 are provided with quick disconnect type couplings 250. Assembly of these wires to the control box and passing them through the opening 244 is facilitated by the above-described arrangement. Specifically, the individual wires are first passed through the enlarged section 248 of the opening 244 and then pulled down into the narrow section 246. Following installation of all of the smaller wires 240, the large electrical service line 242 is passed through the enlarged section 248 of the opening. The service line 242, as is conventional, contains three separate wires, each of which bears the reference numeral 252. It will be noted with reference to FIG. 40 and 42 that only one of the wires 252 is connected to the control switch within the housing. The other two wires 252 of the service cord make a reverse turn as indicated at 254 and pass out through a top section 256 of the enlarged section 248 above the service cord to a location where the quick disconnect couplings 250 carried thereby are attached to the appropriate wires of the air conditioning unit 10.

With all of the wiring thus installed, the front section 190 of the control box 182 is easily attached to the rear section 214 by engaging the two hooks 206 carried by the front section with the mating transverse elements 226 carried by the rear section as indicated in FIG. 40. As thus engaged, the front section 190 is pivoted downwardly and rearwardly to engage the forwardly facing surface 212 carried by the ramp 208 with the rearwardly facing section 234 carried by the transverse section 232 of the flexible latch 230 formed in the bottom wall of the back section 214.

Looking now at FIGS. 42 and 43, strain relief structure for the power service cord 242 is molded directly into the back wall 216 of the back section 214 of the control box 182. This structure comprises a narrow open passage 258 located above the opening 244 which is defined by a lower wall section 260 and an upper wall section 262. Located below the opening 244 and spaced from the opening on opposite sides thereof are a pair of hook-like structures 264 and 266 on the left hand side and the right hand side, respectively, as viewed in FIGS. 42 and 43. The left hand hook 264 defines a power cord receiving space, which is open ended on its right hand side, while the right hand hook 266 defines a power cord receiving space, which is open ended on its left hand side. Each of the power cord receiving spaces defined by the hooks 264 and 266 have a height just slightly greater than the thickness of the power cord 242. Each hook 264 and 266 is provided with a downwardly extending projection 268 at its outer end. In a similar manner, the inside of the upper wall 262 is provided with a pair of spaced downwardly extending power cord engaging extensions 270.

FIG. 43 illustrates the torturous path which the power cord passes in engaging the strain relief structure. Specifically, as the power cord exits the enlarged section 248 of the opening 244, it makes a reverse turn 272 and passes under the space in the right hand hook 266. It then undergoes a ninety degree angle change in orientation and passes through the narrow passage 258 defined by the walls 260 and 262. Passing from the passage 258, it undergoes another ninety degree angle change in orientation where it passes through the space defined by the left hand hook 264. It should be evident from the drawing figures how the projections 268 on the hooks 264 and 265, and the projections 270 on the upper wall 262 serve to retain the power cord within their respective spaces. As thus installed, when the power service cord 242 is subjected to the Underwriter's Laboratories® Pull Test, there is sufficient resistance between the cord and the tortuous path defined above to pass the requirements of this test.

With continued reference to FIGS. 39 through 43, the right side wall 204 of the front section 190 of the control box 182 includes a lateral extension 272 thereof, which defines an upwardly facing surface 274 and a downwardly facing surface 276. Extending from the downwardly extending surface 276 is a substantially vertically extending integrally molded pin 278. A second pin 280 in axial alignment with the pin 278 is mounted on the upwardly facing surface 274. The pin 280 is mounted to a flexible arm 282, which is attached near the front of the surface 274 and which extends upwardly and rearwardly to support the upper pin 280 at a position spaced from the surface 274 as indicated by the space 284. This structure allows the flexible arm 282 and the pin 280 carried on the upper side thereof to be flexed downwardly from its normal position as illustrated in the drawing figures. The left hand side wall 202 of the front section 190 is provided with a rearwardly extending flexible latch 286, which has a vertically extending forwardly facing latching surface 288 formed thereon. The latch is deflectable by depressing it to the right thereof.

The control box 182 as thus assembled is attached directly to mating structure provided in the upper right hand corner of the indoor housing 44 as illustrated in FIG. 10. This mating structure is illustrated in FIGS. 10 through 13 and includes a pair of forwardly facing mounting arms 290 integrally molded with the indoor housing 44 in the upper right hand corner thereof. The arms are vertically spaced from one another and are provided with openings 292 in their outer ends, which are adapted to engage the pins 278 and 280 on the control box.

Figure 39:
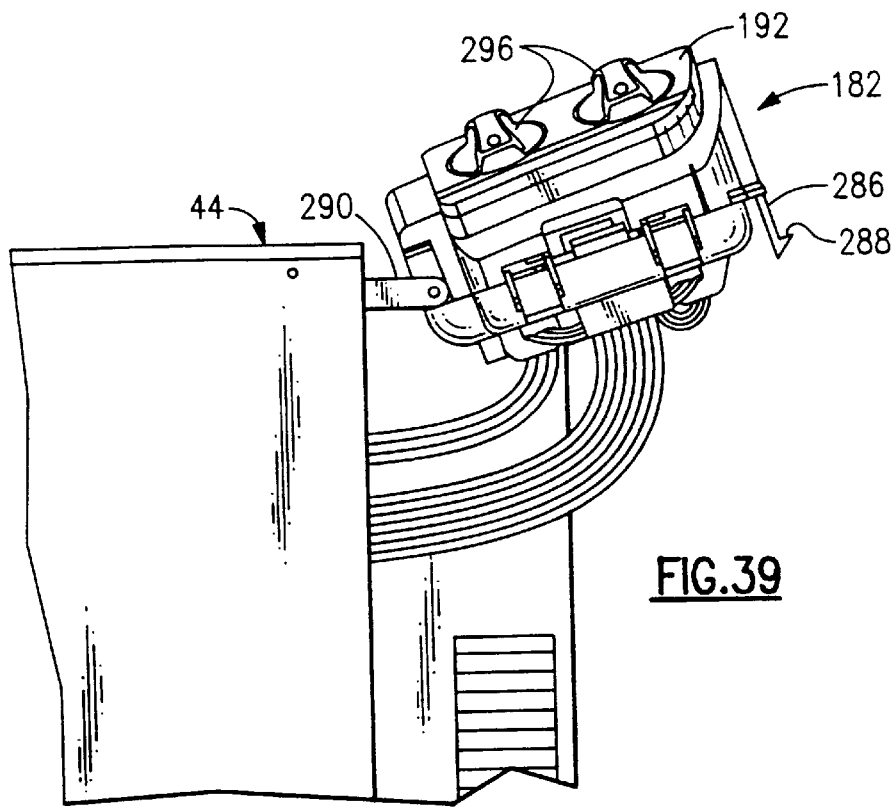
FIG. 39 is a simplified plan view of the right hand front corner of the indoor module showing the control box in a preliminary assembly position on the evaporator housing.

Accordingly, installation of the control box is achieved by engaging downwardly extending pin 278 with the opening 292 in the lower mounting arm 290. The flexible arm 282, which carries the upper pin 280 is deflected downwardly to thereby allow the upper pin 280 to engage the opening 292 in the upper control box mounting arm 290. The box as thus assembled is illustrated in FIG. 39. Assembly of the control box to the indoor housing 44 is then achieved by pivoting the control box towards the housing without its pivotal mounting until the latch 286 and the forwardly facing surface 288 snap into a vertically extending latching surface 294 provided in the indoor housing 44 as shown in FIG. 11. Control knobs 296 are assembled to the shafts 298 of the control switch 184 and the thermostat 186 to complete the control box assembly. The control knobs are uniquely adapted to be assembled to the control shafts as a single piece component without any additional internal structure while maintaining a positive operational attachment to the shafts as will be described in detail hereinbelow.

Figures 36, 37, 38:
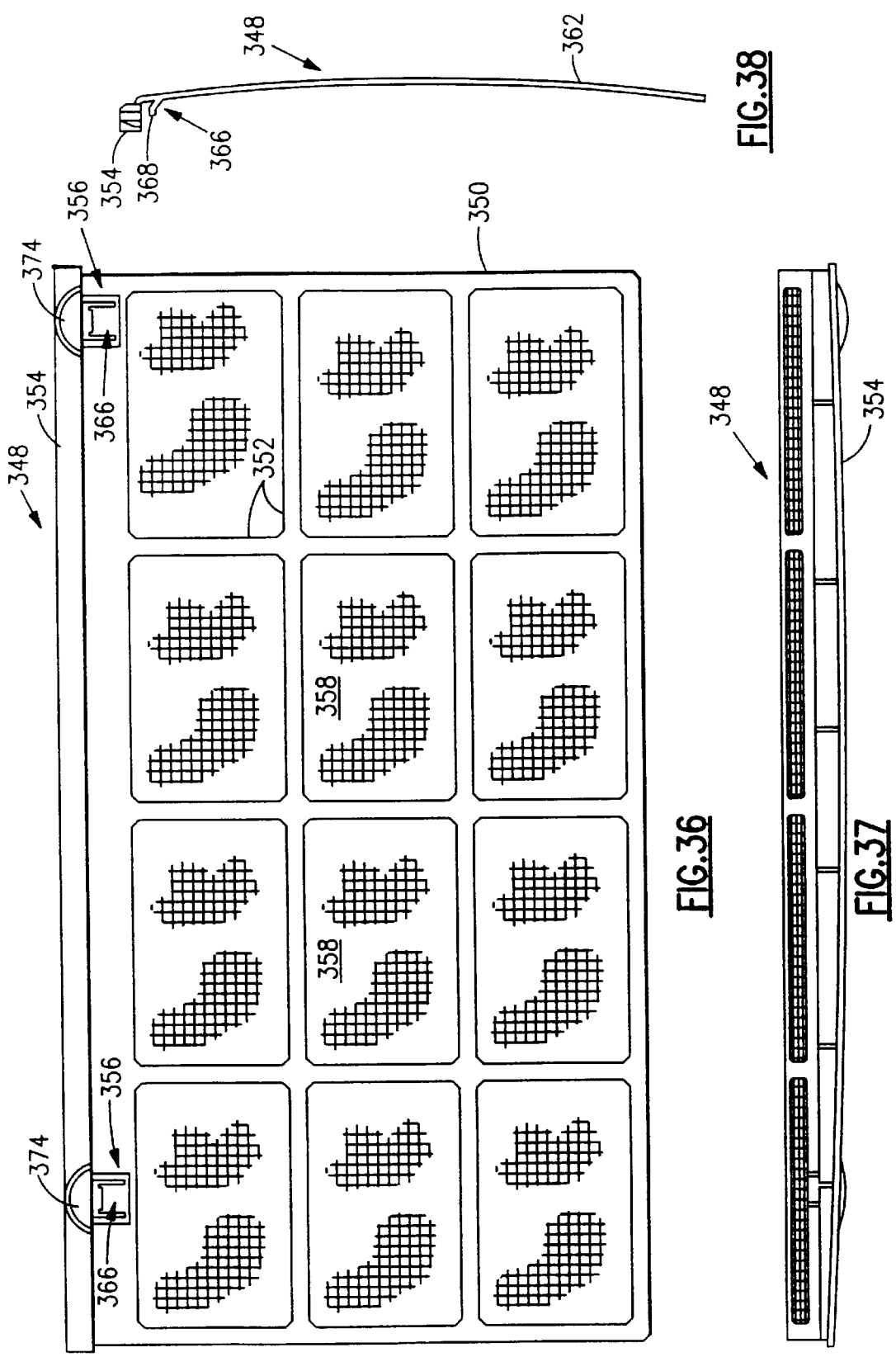
FIG. 36 is a front plan view of the snap-in filter.
FIG. 37 is a top plan view of the filter shown in FIG. 36.
FIG. 38 is left side view of the filter shown in FIG. 36.

The front grille 24 of the indoor module 12 is provided with an indoor air filter unit 348, which is illustrated in FIGS. 36 through 38. The indoor grille 24 and its installation to the indoor housing 44 will first be described followed by a detailed description of the filter unit 348 and its installation in the front grille. With reference now to FIGS. 27 through 31, the front grille 24 includes a substantially planar front section 302 which includes inlet louvers 22 and an opening 304 in which the indoor air discharge assembly 26 is mounted. The front section 302 also includes a substantially rectangular opening 306 which is adapted to receive the control box assembly 182 therein when the grille 24 is mounted to the air conditioning unit.

Figure 27:
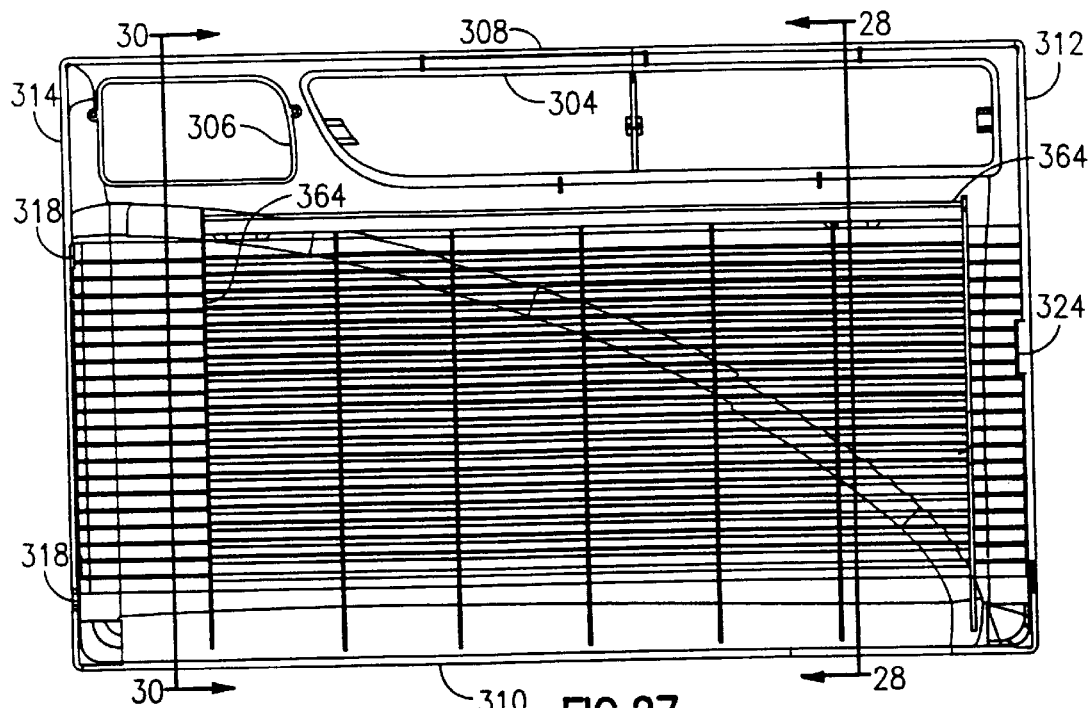
FIG. 27 is a rear elevational view of the indoor module front grille.

Extending from the planar front 302 are a top wall 308, a bottom wall 310 and left and right hand side walls 312 and 314, respectively. The top, bottom, left and right walls cooperate to define a shirt element integrally formed and extending rearwardly from the planar front 302 of the grille 24. It should be understood that FIG. 27 illustrates the back of the inlet grille 24. The references to left and right hand sides are based on viewing the air conditioning unit and grille 24 from the front as illustrated in FIG. 1 and, accordingly, references to left and right are reversed with respect to FIGS. 27 through 31.

Figure 28:
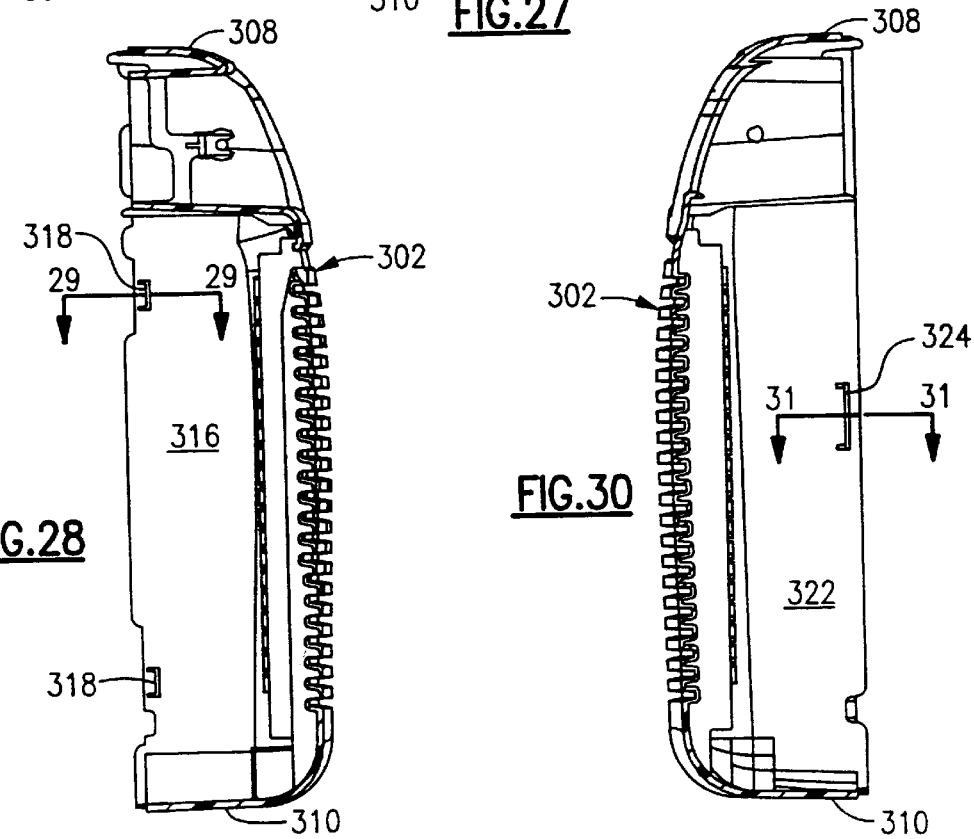
FIG. 28 is a sectional view taken along the lines 28—28 of FIG. 27.

Looking now at FIG. 28, the inside wall 316 of the right wall of the grille 24 is shown. Integrally formed in this wall is a pair of transverse extending raised formations 318, each defining a forwardly facing planar surface 320.

Figure 30:
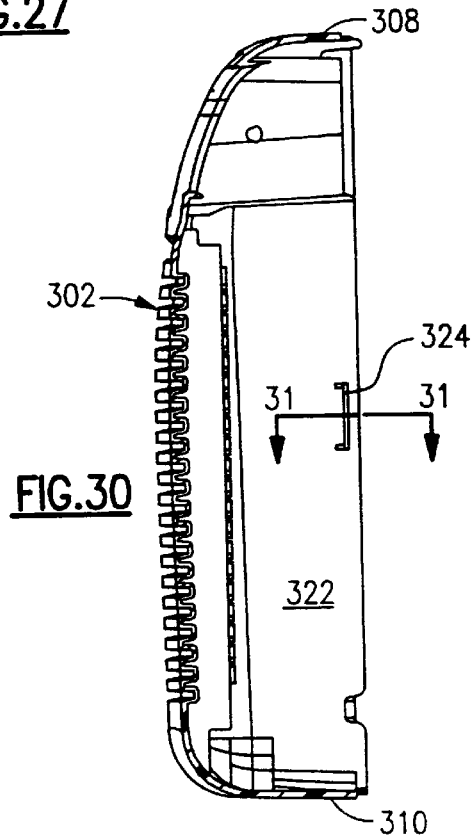
FIG. 30 is a sectional view taken along the lines 30—30 of FIG. 27.
Figure 29:
FIG. 29 is a sectional view taken along the lines 29—29 of FIG. 28.
Figure 31:
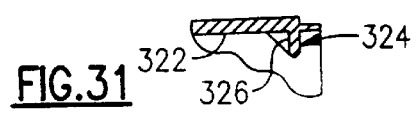
FIG. 31 is a sectional view taken along the lines 31—31 of FIG. 30.

With reference to FIGS. 30 and 31, the inside wall 32 of the left hand wall 312 is provided with a transversely extending latch engaging structure 324. The latching structure 324 defines a forwardly facing planar latching surface 328.

The front grille 24 is adapted to be mounted directly to mating structures provided on the indoor housing 44. With reference to FIGS. 10, 11 and 12, the right wall 54 of the indoor housing 44 is provided with a pair of integrally molded spaced apart grille mounting extensions 330. Each extension extends forwardly of the inside of the wall 54 and is provided with a longitudinally extending opening 332, which is adapted to receive the raised formations 318 on the right wall of the grille such that the forwardly facing walls 320 are operatively engaged in planar confronting relationship with a mating surface in the recess 332 in which it is received.

Figure 15:
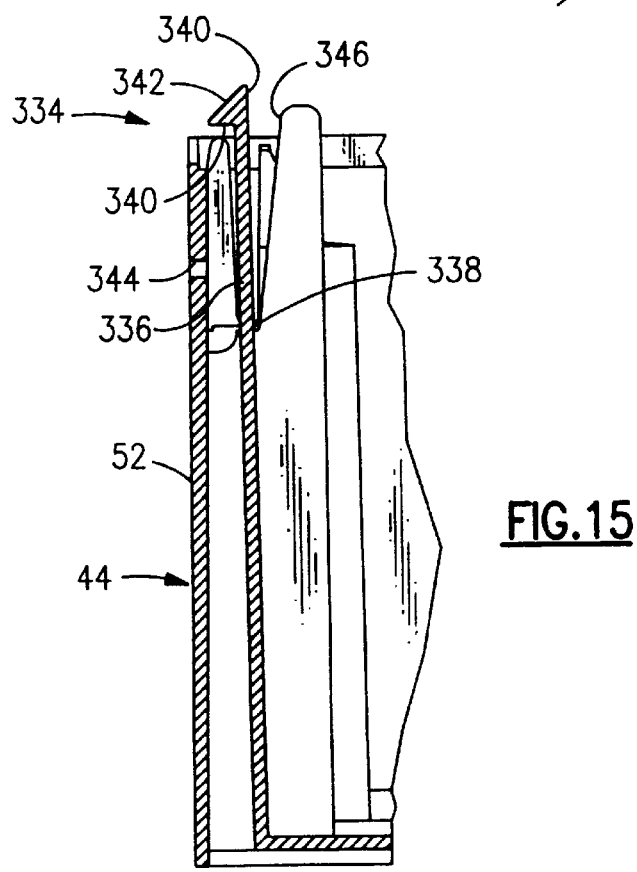
FIG. 15 is a sectional view taken along the lines 15–15 of FIG. 11.
Figure 32:
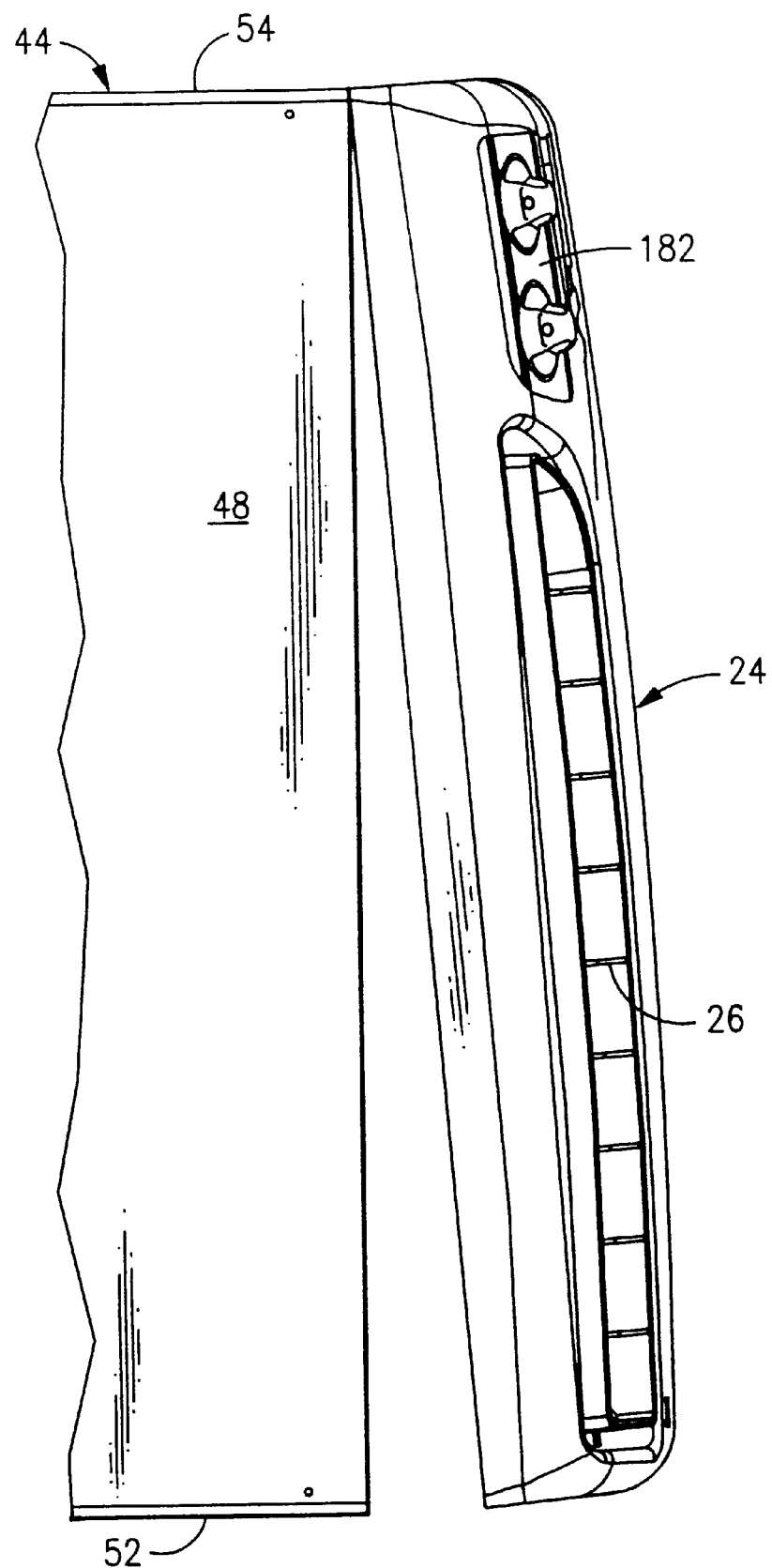
FIG. 32 is a simplified partial plan view of the indoor module illustrating the method of attachment of the indoor grille thereto.

The latching structure 324 on the left wall 312 of the grille is adapted to receive a latch mechanism 334 formed on the inside of the left hand wall 52 of the indoor housing 44. The latch mechanism 334 is best illustrated in FIGS. 11, 12 and 15. The latch 334 includes a flexible arm 336 integrally formed with the housing 44. The arm 336 extends from a fixed portion 338 and extends outwardly to a outer end 340, which includes a rearwardly facing latching surface 340. The latching surface 340 is adapted to engage the forwardly facing latching surface 328 formed on the left side wall of the grille 24 when the grille is attached thereto. The latch includes an inclined surface 342 which is adapted to facilitate engagement of the grille 24 with the housing 44 to deflect the latch as the grille and housing are moving into operative engagement Installation of the indoor grille 24 to the housing 44 is accomplished by orienting the indoor grille as illustrated in FIG. 32. As shown, the two raised formations 38 on the right hand wall of the grille have been operatively engaged with the mating openings 332 and the mounting extensions 330. This engagement provides a pivot point which fixes the right hand side of the grille and allows pivotable motion thereabout to move the left hand side towards the indoor housing 44. Continued movement of the left hand side of the grille towards the housing results in engagement of the inclined surface 342 with the latching structure 324 which then results in inward deflection of the flexible arm until the grille is moved rearward into its desired installed position where the end 338 of the latch 334 moves into positive engagement with the forwardly facing wall 328 to thereby positively attach the front grille 24 to the housing 44.

With reference to FIG. 15, removal of the grille from the housing is accomplished by inserting a small tool (not shown) through an opening 344 which is provided in the left side wall 52 of the housing 44 adjacent the flexible arm 336. Force exerted on the tool results in the flexible arm deflecting inwardly thereby releasing the latch mechanism 334. In order to prevent breakage of the flexible latch arm, an integral stop surface 346 is integrally molded into the housing 44 behind the latch. The flexible arm 336 engages the stop surface 346 prior to reaching its breaking point thereby protecting it from inadvertent breakage during the removal of the grille.

With reference now to FIGS. 33 through 38, a filter assembly 348 is provided to filter the indoor air passing through the inlet openings 22 in the indoor grille 24 before it passes to the evaporator coil 18. The filter includes a substantially rectangular frame 350, which defines a curved grid-like section 352. The top of the filter frame 350 defines a horizontally extending forwardly facing wall 354 which has a pair of manually releasable snap fit latch confirmations 356 provided at opposite ends thereof. The filter frame 350 is preferably made from an unfilled copolymer polypropylene. A filter screen material 358 overlies and is integrally attached to the sections forming the grids 352. This screen is preferably a polypropylene material and is adapted to be cleaned by vacuuming and/or washing so that it may be reused for the lifetime of the unit.

The filter 348 is adapted to be received in a horizontally extending opening 360 provided in the front inlet grille 24 at the upper end thereof above the inlet louvers 22. As is best seen in FIG. 34, the filter is adapted to be inserted into the slot 360 with the outwardly curved side 362 facing the back of the unit 10. As the filter is inserted through the slot, the back side 362 slides directly against the evaporator coil 18 and the unit is guided laterally by side walls 364 extending from the inside wall of the grille 24. The side walls are illustrated in FIG. 27. When fully inserted, the filter completely overlies the evaporator coil and the wall 354 covers the opening and forms a part of the front surface of the grille 24.

As installed, the latch mechanisms 356 engage mating structure provided on the lower edge of the horizontal slot 360 as will now be described. The latch mechanisms on the screen 356 each comprise an upwardly and forwardly extending flexible latch 366 integrally formed with the filter frame 350. Free ends 368 of the latches are adapted to be engaged in small horizontally extending slots 370 formed in the lower wall 372 of horizontal slot 360. A semi-circular recess 374 formed in the filter wall 354 adjacent each of the latches 366 and a mating arcuate recess 376 is provided in the wall 372 adjacent to the horizontal slots 370.

Accordingly, when the filter is installed to the air conditioner as described above, the flexible latches 366 in the filter will be deflected rearwardly such that the free ends 368 of the latches engage the horizontal slots 370 in the lower wall 372 of the slot. This positively retains the filter in its operative position. When it is desired to remove the filter for cleaning, the free ends 368 of the latches are readily accessible as a result of the arcuate recesses 374 and 376 therearound, to be manually depressed to release them from the horizontal slot 360. At the same time, the arcuate recess 374 serves as a grip for manually removing the filter 348 from the slot. With reference to FIG. 37, it should be noted that the top wall 354 of the filter frame 350 is asymmetrical. This allows the top forward wall to conform with the front wall of the grille to cover the slot, which is displaced to the left hand side of the curved forward wall of the grille 24.

As previously briefly described in connection with the description of the control box 182, the knobs 296 adapted for engagement on the shafts 228 of the control switch 184 and 186 are molded as a single component without requiring any additional inserts or clips or the like to facilitate positive operative engagement with their associated shafts 228. In the preferred embodiment, the control knobs 296 are molded from an ABS plastic material.

With reference to FIGS. 44 through 49, the knob is round and has a pair of planar sections 377, which are separated by a large outwardly extending conformation 378 on the outer side thereof, which is adapted to be grasped manually to rotate the knob. This conformation extends from a larger dimension at one end 380 thereof, tapers to a smaller dimension at the mid-section 38 thereof, and then expands at the other side thereof 384 back to the larger dimension. The conformation comprises an outer wall 386 and a pair of arcuately shaped side walls which extend from the outer wall 386 to one of the planar section 377.

The back of the knob 296 is provided with a large recess 390, which conforms substantially in shape to the outwardly extending conformation 378 on the upper side of the knob. Specifically, the recess has a lower wall 392, which is the opposite side of the outer wall 386 and curved side walls 394, which are the inner walls of the curved side walls 388 of the conformation 378. Centrally located with the recess 390 is a shaft receiving structure 396, which defines a D-shaped opening 398. The shaft receiving structure 396 and the D-shaped opening therein 398 are separated into two spaced apart sections by a vertically extending slot 400. Each separate section of the shaft receiving structure is integrally formed with the curved side wall 394 as represented by reference numeral 402.

With reference specifically to FIGS. 45, 46 and 47, it will be noted that the D-shaped opening 398 is molded with a negative draft angle. This results in the cross sectional area of the opening at the outer end 404 being smaller than the cross sectional area 406 at the lower end thereof. The size of the opening 404 at the upper end is such that the tapered end 408 of the shaft as illustrated in FIGS. 48 and 49 will be just received therein.

The thickness of the curved walls 388/394 are formed such that when the shaft 228 is inserted at the upper end 404 of the D-shaped opening, and as the full dimension shaft section 410 is inserted therein, the two separate sections of the D-shaped opening and the arcuate wall section 388/394 to which they are integrally attached at 402, will flex outwardly. This results in an increase in the cross section of the opening 298, which thus allows full insertion of the shaft. As a result, once the knob has been installed on a shaft 288, the walls 388/394 and the separate sections of the D-shaped openings will be attempting to return to their undeformed condition and, as a result, exert a firm engagement on the full dimension portion 410 of the shaft 228.

It will be noted that an upwardly extending stop 412 is molded into the lower wall 392 of the recess 390 to limit penetration of the shaft to the desired position. It should be further appreciated that the thickness of the curved walls 388/394 and the thickness of the planar sections 377 to which these walls are attached is extremely important in allowing the desired flexibility described above. Selection of such thicknesses is within the purview of one skilled in the art and will vary depending on the material used, the size of the shaft and other variables.

Figure 51:
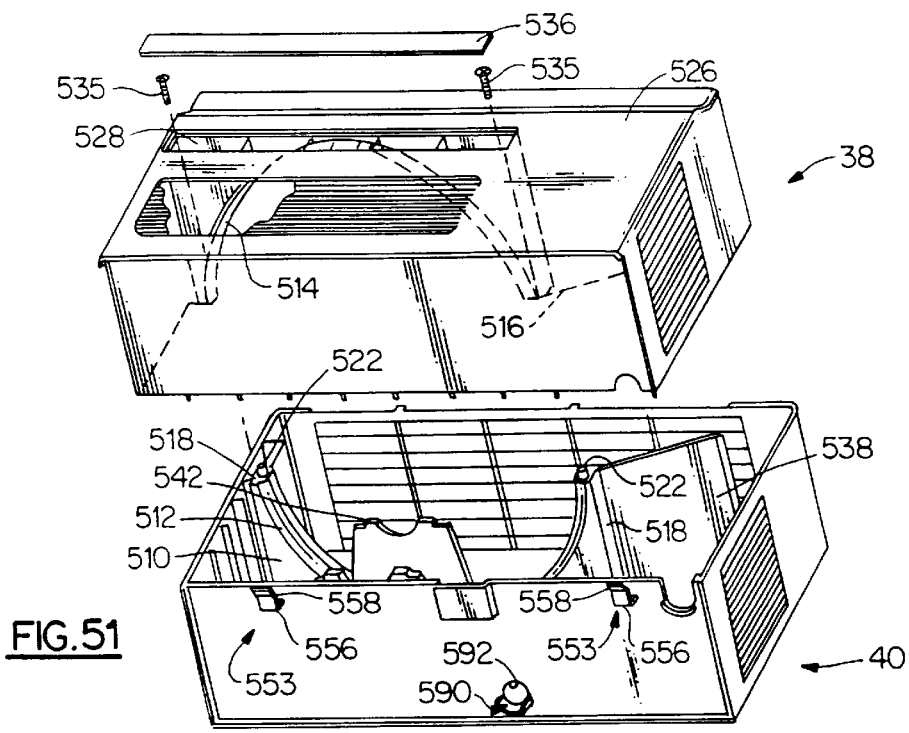
FIG. 51 is a perspective view of the upper and lower sections of the outdoor module, unassembled and spaced from one another to show internal components thereof.
Figure 52:
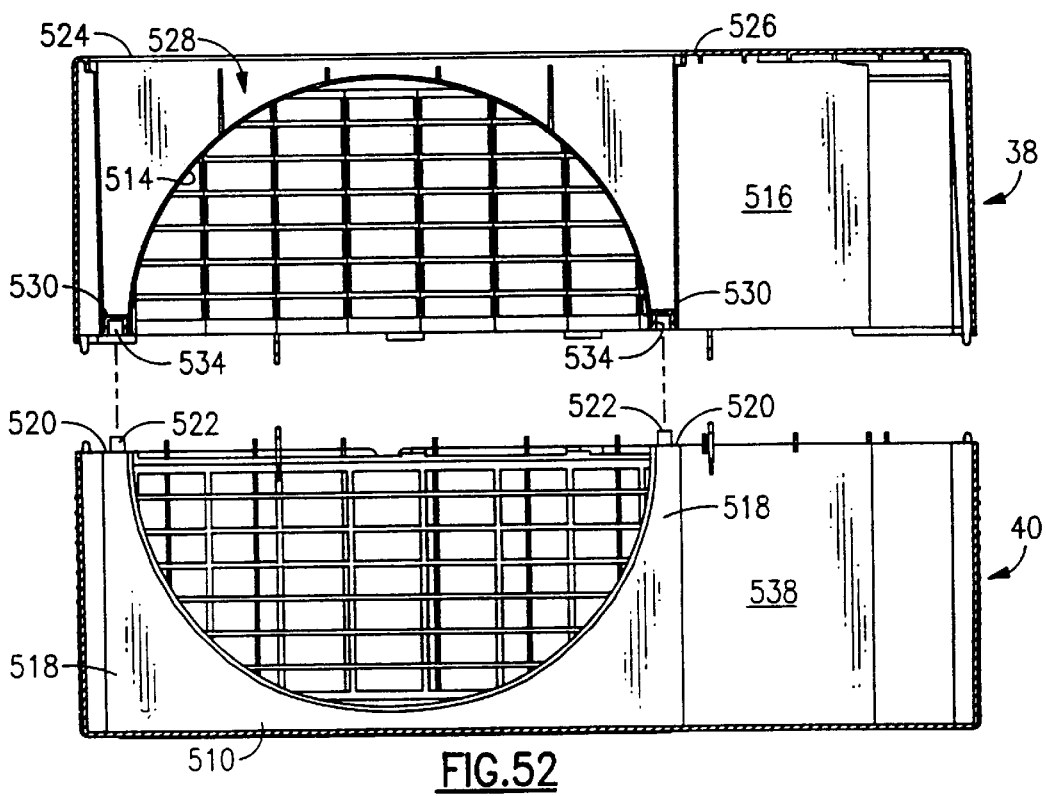
FIG. 52 is a back view of the upper and lower sections of the outdoor module housing.
Figures 57, 58:
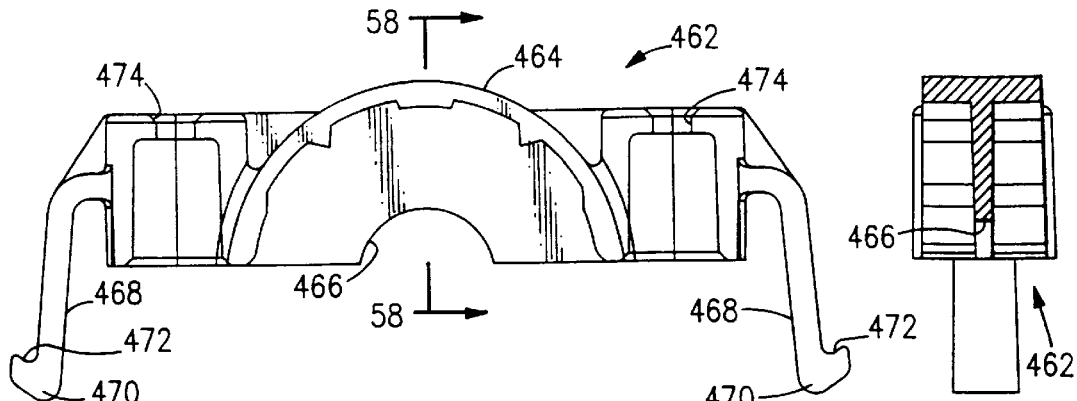
FIG. 57 is a side view of the outdoor fan motor mounting clip.
FIG. 58 is a sectional view taken along the lines 58—58 of FIG. 57.
Figure 59:
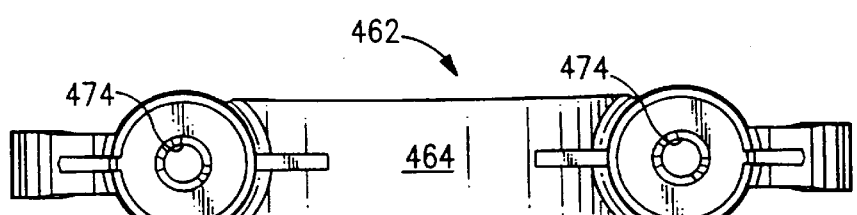
FIG. 59 is a top plan view of the motor mounting clip of FIG. 57.
Figure 60:
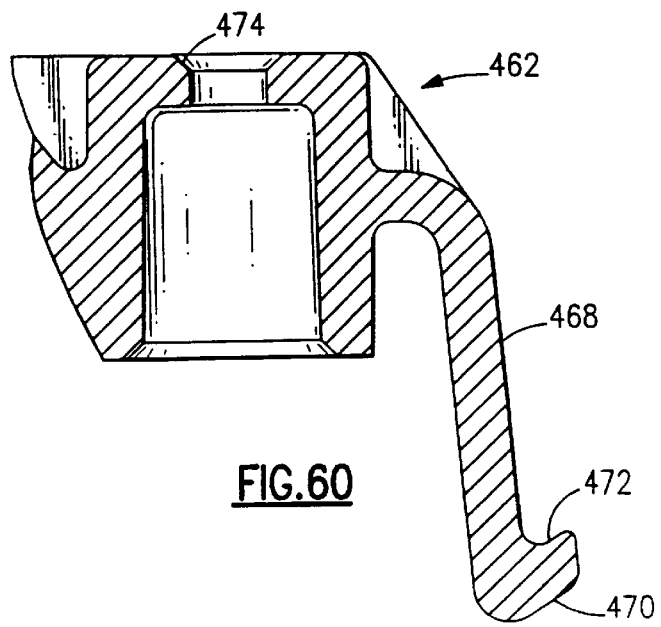
FIG. 60 is an enlarged sectional view of the right hand latch of the clip of FIG. 57.

The outdoor module 14, as briefly described in connection with FIG. 2, will now be described in detail. FIGS. 51 and 52 illustrate in more detail the upper 38 and lower 40 sections of the outdoor module housing. Each of these sections is molded in a single part from a suitable structural plastic material.

As illustrated in FIGS. 3, 10, 50 and 54 through 56, structure for mounting of the compressor 34 is integrally molded directly into the lower wall 414 of the lower part 40 of the outdoor housing. The compressor 34 has a triangular mounting plate 416 attached thereto. The mounting plate 416 has openings at each of the three corners thereof to facilitate attachment to the lower wall 414 through the mounting structure of the invention. Three substantially identical mounting structures 420 are provided, one associated with each of the openings in the plate. Only one of these will be described in detail. However, it should be understood that according to an important aspect of the invention, the orientation of each of the mounting structures with respect to the other two is critical with respect to the invention. Each mounting structure 420 comprises a raised elliptically shaped portion 422 in which is molded a vertically extending compressor mounting stud 424. Associated with each stud 424 is a vertically extending arcuately shaped projection 426. The arcuate projections 426 are oriented at a location spaced from their associated stud 424 in a direction towards the two adjacent studs and each encompass an angle at least as large as the angle defined by a pair of lines 428 drawn between the associated stud 424 and its two adjacent studs. The height of the arcuate sections 426 is less than that of the studs 424.

Mounting of the compressor and mounting plate is accomplished by first assembling elastomeric isolator bushings 430 to each of the three openings 418 provided in the compressor mounting plate 416 as illustrated in FIG. 56. The mounting plate 416, with the compressor mounted thereupon, is then set in place with the three integrally formed studs 424 extending through axially aligned openings 432 provided in each of the elastomeric bushings 430. The diameter of the elastomeric bushings is such that when the studs 424 are received therein, the outer circumference 434 of each bushing is in close contact with the inner surface of the arcuate wall 426 associated with the stud to which the bushing has been engaged.

A single "fender" washer 436 is then placed over each of the bushings with its central opening in alignment with an opening 438 which has been molded integrally into each of the studs 424. A simple sheet metal screw 440 is then threaded directly into the opening 438 in the stud and tightened to a predetermined torque to avoid stripping of the threads formed within the openings as the screw is attached thereto.

The compressor is thus mounted through the mounting plate 416 to the integrally formed studs 424 in a manner such that movement of the compressor in any direction is absorbed by or reacted through the elastomeric bushing. Specifically, in the radial direction, forces are reacted through the bushings 430 directly to the arcuate walls 426 associated with each stud to thereby substantially reduce lateral forces on the upstanding studs 424.

In a specific embodiment, each of the arcuate walls encompasses an arc of 106°. It should be appreciated that as such, radial movement of the compressor in any direction will then be absorbed and reacted by one or more of the elastomeric bushing/arcuate wall combinations.

As best shown in FIGS. 3, 51, 53 and 54, the outdoor fan motor 32 is mounted to a pedestal type mounting structure 440, which is integrally molded into the lower wall 414 of the lower section 40 of the outdoor housing. The motor support comprises a first pair of substantially vertically extending spaced legs 442 directly formed at their lower end 444 with the lower wall 414. At the upper ends 446 thereof, the vertical legs 442 make a transition through a horizontally extending section 448 to a second pair of vertically extending legs 450, which are oriented substantially perpendicular to the first pair of legs 442.

The upper ends 452 of each of the legs 450 are spaced from one another a distance substantially equal to the axial length of the outdoor fan motor 32. As best seen in FIGS. 51 and 54, the upper end 452 of each of the legs 450 defines an upwardly extending surface, which is provided with a centrally positioned semicircular shaped support recess 454 adapted to receive mating mounting bushings 456 on the opposite axial ends of the motor. Spaced outboard of and on opposite sides of the motor receiving recess 454 are openings 458. As seen in FIG. 54, the molded motor mount has a thickness such that the openings communicate with the hollow interior and define a horizontal downwardly facing latching surface 460 associated with each of the openings 458.

Mounting of the outdoor fan motor 32 with the fan 30 assembled thereto is accomplished by positioning the bushings 456 at the axial opposite ends of the motor into the receiving structure 454 in the upper ends 452 of the legs 450. Following this, motor mounting clips 462, illustrated in detail in FIGS. 57 through 60 are assembled to the motor mount 440 to secure the motor thereto in its final operative position.

Each of the motor mounting clips 462 is formed as a single piece from a plastic material, preferably ABS 21. Each of these clips comprises a horizontally extending central section 464, which has a semicircular shaped recess 466 formed therein adapted to engage the upper side of the motor bushings 456. Carried on the outer ends 468 on the horizontal section 464 are a pair of downwardly extending flexible arms 468, each of which carries a latching structure 470 at the end thereof. The latching structures each define an upwardly facing latching surface 472. The horizontal section 464 of the mounting clips 462 are also provided with a second pair of openings 474 therethrough on opposite sides and directly adjacent to of the arcuately shaped motor engaging section 466.

The flexible arms 466 and the latching confirmations are positioned such that when the motor mounting clip is positioned over the upper ends of one of the upper ends of the legs 452, with the motor engaging surface 466 overlying the motor bushing 456, the clip may be installed to the motor mount by deflecting the two flexible arms 468 inwardly until the latching confirmations 470 enter the openings 458. Once in place, and engaging the motor bushing, the latching arms may be released and the upwardly facing surfaces 472 will engage the downwardly facing surfaces 460 adjacent the openings 458 to positively retain the motor mounting clip 462 and thus the motor fan assembly in its desired operative position.

In the event that the flexible arms should be broken in the future, due to servicing or trauma to the air conditioning unit, attachment of the motor clips 462 to the upper ends 452 of the motor mount may be achieved by passing suitable threaded fasteners through the openings 474 in the clip and into suitable openings provided in the upper ends 452.

Also mounted in the lower housing 40 of the outdoor section is a large cylindrical metal encased capacitor 476 for both the compressor motor and the outdoor fan motor. With reference to FIGS. 3, 54 and 61 through 63, it will be noted that the capacitor receiving support structure 478 is molded integrally into the lower wall 414 of the lower outdoor housing 40. The support is located directly adjacent to and molded directly into the rear wall of the lower housing 40. Directly above the capacitor support 48 and molded into the other side of the rear wall 480 is a rectangular opening 482 and a forwardly extending wall section 484 extending beyond the opening 482 on the lateral sides thereof to define a pair of vertically extending slots 486, one on each side of the opening between the front wall 480 and the wall extension 484.

Figure 63:
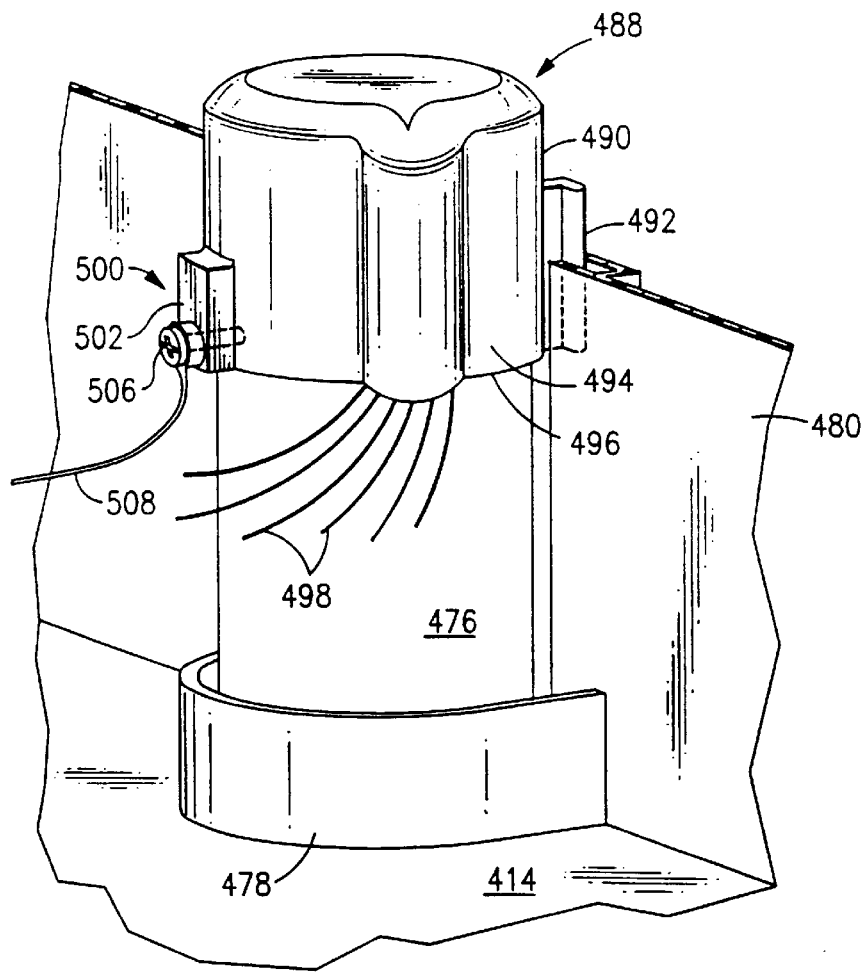
FIG. 63 is an enlarged perspective illustration showing the mounting arrangement of the outdoor capacitor.
Figure 62:
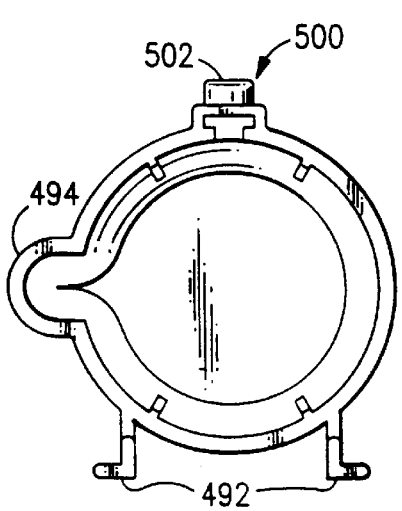
FIG. 62 is a sectional view taken along the lines 62—62 of FIG. 61.
Figure 61:
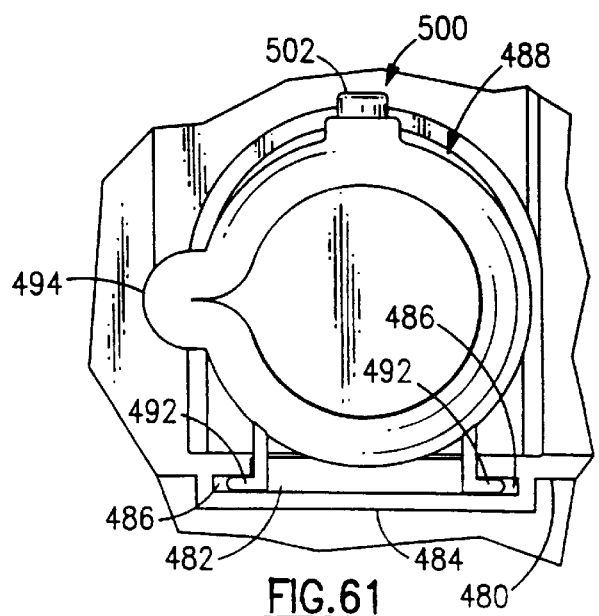
FIG. 61 is an enlarged view of the outdoor capacitor mounting arrangement as illustrated in FIG. 3.

The capacitor 476 has a plurality of electrical leads attached to the upper end thereof is thus adapted to be placed within capacitor support 478 as illustrated in FIG. 63 and a capacitor cover 488 installed thereover. The capacitor cover 488 comprises a substantially cylindrical element 490 having an inside diameter just slightly larger than the outside diameter of the capacitor 476, which it is protecting. Extending radially outwardly from the outer cylindrical surface 490 of the capacitor cover are a pair of vertically extending L-shaped legs 492. The legs 492 extend beyond capacitor cover a distance to allow them to be received in the vertically extending slots 486 described above. The legs 492 and the vertically extending slots 486 are sized such that the capacitor support 478 and capacitor cover 488 may cooperate to accommodate capacitors of varying heights while still providing protection to the upper end and the terminals of the capacitor. The engagement between the L-shaped legs 492 and the receiving spaces 486 is such as to assure frictional retention of the cover 488 once it is installed.

Also radially extending from the cylindrical capacitor cover 490 is a vertically extending surface 494 defining a vertical passageway from the upper interior of the capacitor cover to the open end 496 thereof. As seen in FIG. 63, this allows passage of the multiple electrical leads 498 from the capacitor to the various electrical components of the unit.

Also radially extending from the cylindrical capacitor cover 490 is a rectangular extension 500 of sufficient thickness to have a threaded opening 502 formed therethrough which extends from an outer surface 504 thereof to the interior of the cover. As seen in FIG. 63, the threaded opening is adapted to receive a grounding screw 506 therethrough, which is attached to a grounding wire 508. The screw is adapted to electrically contact the outer metallic cover of the capacitor 476 to thereby provide grounding thereof.

With reference now to FIGS. 3, 10, and 50 through 52, it will be noted that also directly molded into the lower wall 414 of the lower outdoor housing 40 is a structural wall 510. The wall 510 includes a semicircular opening 512 therethrough. The opening 512 cooperates with a similar opening 514 formed in a downwardly extending structural wall 516 molded integrally into the upper portion 38 of the outdoor housing to define a shroud for the outdoor fan. Opposite sides of the opening 512 in the lower wall 510 are defined by vertically extending structural sections 518, each of which has an upwardly facing planar surface 520 at the upper end thereof. The surfaces 520 have alignment pins 522 extending upwardly therefrom, each of which is provided with an opening therein.

As best seen in FIGS. 51 and 52, the upper housing 38 is provided with a rectangular opening 524 in the top surface 526 thereof. This opening communicates with an arch-shaped space 528 above the wall forming the opening 514. At the lower end 530 of the opposite legs of the arch-shaped space 528, the housing 38 includes a pair of structural attachment points, each having a cylindrical opening 532 therein adapted to receive one of the pins 522 extending from the surface 520. Through openings 534 are provided in the attachment sections 530 to thereby facilitate receiving of a threaded fastener 535 through the respective openings 532 and into the openings in the pins 522 to thereby structurally attach the upper outdoor housing 38 to the lower housing 40 when the air conditioning unit is assembled. Following such assembly, a rectangular filler 536 is adapted to snap fit into the opening 524.

Looking back now at FIG. 3 and 51, the wall 510 in the lower section includes a diagonally extending structural extension 538, which terminates at a free end adjacent one end of the condenser coil 28. Carried at this end of the wall extension 538 are two vertically extending wall sections, generally, 540, which define an open corner which is adapted to receive and position one of the tube sheets 542 of the condenser coil 28. Likewise, the tube sheet 546 at the other end of the condenser coil is supported by a similar structure 548. In a like manner, vertically extending support structure is provided for the back edge of both of the tube sheets 542 and 546. As a result, installation of the condenser coil 28 is a simple matter of vertically lowering the condenser coil 28 into position using the above-described vertical support surfaces as a guide.

Corresponding similar structure is provided within the upper outdoor housing 38 such that the upper housing may be installed to the lower housing as described above once the condenser coil has been positioned in the lower housing. Such assembly results in positive retention of the condenser coil 28 in its desired location without the need for any mechanical fasteners.

It should be appreciated that as a result of the fact that the support for the outdoor fan motor 32 and outdoor fan assembly, and the wall 510, which defines the lower part of the fan shroud and which positions the upper part of the fan shroud, are integrally molded into the same component that the clearance between the outdoor fan 30 and the shroud defined by the openings 512 and 514 may have extremely close tolerances which results in significant improvement in the overall operating efficiency of the unit.

As previously indicated, the air conditioning unit 10 of the present invention may be used as a room air conditioner wherein the indoor module 12 and the outdoor module 14, described in detail hereinabove, are integrally attached to one another and mounted in a metal base pan 16. As will be appreciated, assembly of the indoor module to the outdoor module is extremely simple. The sequence of assembly is to first assemble the outdoor module 14 with the upper housing 38 removed therefrom as illustrated in FIG. 10. With the upper cover 38 removed, the refrigeration tubes 164 and the appropriate electrical wiring 240 from the control box may be passed through an opening 550 in the front wall of the outdoor housing defined in part by a semicircular opening 552 in both the upper and lower housings 38 and 40.

Attachment of the indoor and outdoor modules is achieved by aligning a pair of structural hooks 553 molded into the front wall 480 of the lower housing 40 with mating openings 554 structurally molded into the rear wall 46 of the indoor housing 44. As best shown in FIGS. 2 and 51, the hooks 553 comprise a substantially vertically extending section 556 with a rearwardly extending inclined section 558. This arrangement facilitates ease of assembly by allowing the indoor module 12, to be positioned adjacent to and vertically above the outdoor module with the openings 554 thereof, above and aligned with the hooks 553. Engagement of the hooks 553 and openings 554 is then achieved with a simple downward force on the indoor module 12.

Following such assembly, the appropriate interconnections of the refrigerant tubing 164 and electrical wires 240 may be made. Following this, the upper section 38 of the outdoor housing is installed on the unit by vertically orienting it directly over the lower section 40 and lowering it downwardly into place with guidance being provided by the rear wall 46 of the indoor housing 44. It will be appreciated that as the upper housing 38 is lowered into place, the support structure 548 carried thereby to support the upper portion of the condenser coil 28 will engage the coil. Also, the above-described engagement of the alignment pins 522 and the openings 534 on opposite sides of the fan shroud move into engagement so that the threaded fasteners 535 may then be installed to complete attachment of the upper housing 38 to the lower housing 40. Suitable alignment structure, generally, 560 is provided on the back side of both the upper and lower housings in the region of the outdoor discharge louvers 42. This structure will not be described in detail and simply provides alignment of the flexible back wall portion of the unit when the housings are assembled to one another.

Following this, the rectangular filler 536 is snapped into the rectangular opening 524 in the top 526 of the outdoor housing 38. Further interconnection is provided by a pair of threaded fasteners passing through a pair of openings 564 in a lip 566, which extends forwardly from the top 526 of the upper housing 38. The lip 566 overlaps a mating recess 568 in the top wall 48 of the indoor housing 44 and passes through openings 570 provided therein to complete the interconnection of the indoor and outdoor modules.

Figure 50:
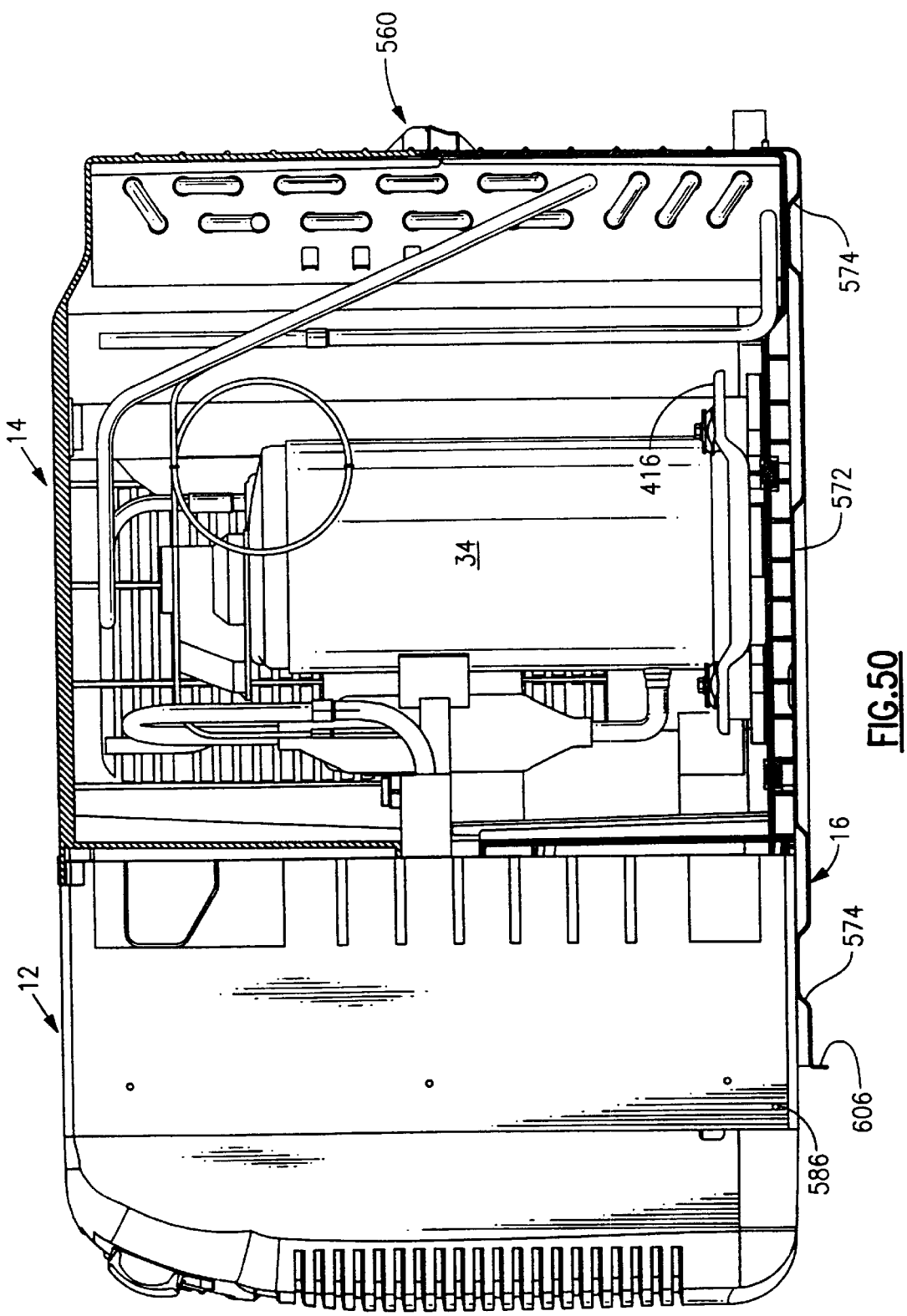
FIG. 50 is a right side view of the air conditioner of FIG. 1 with the side wall of the outdoor module broken away to show the internal components thereof.
Figure 64:
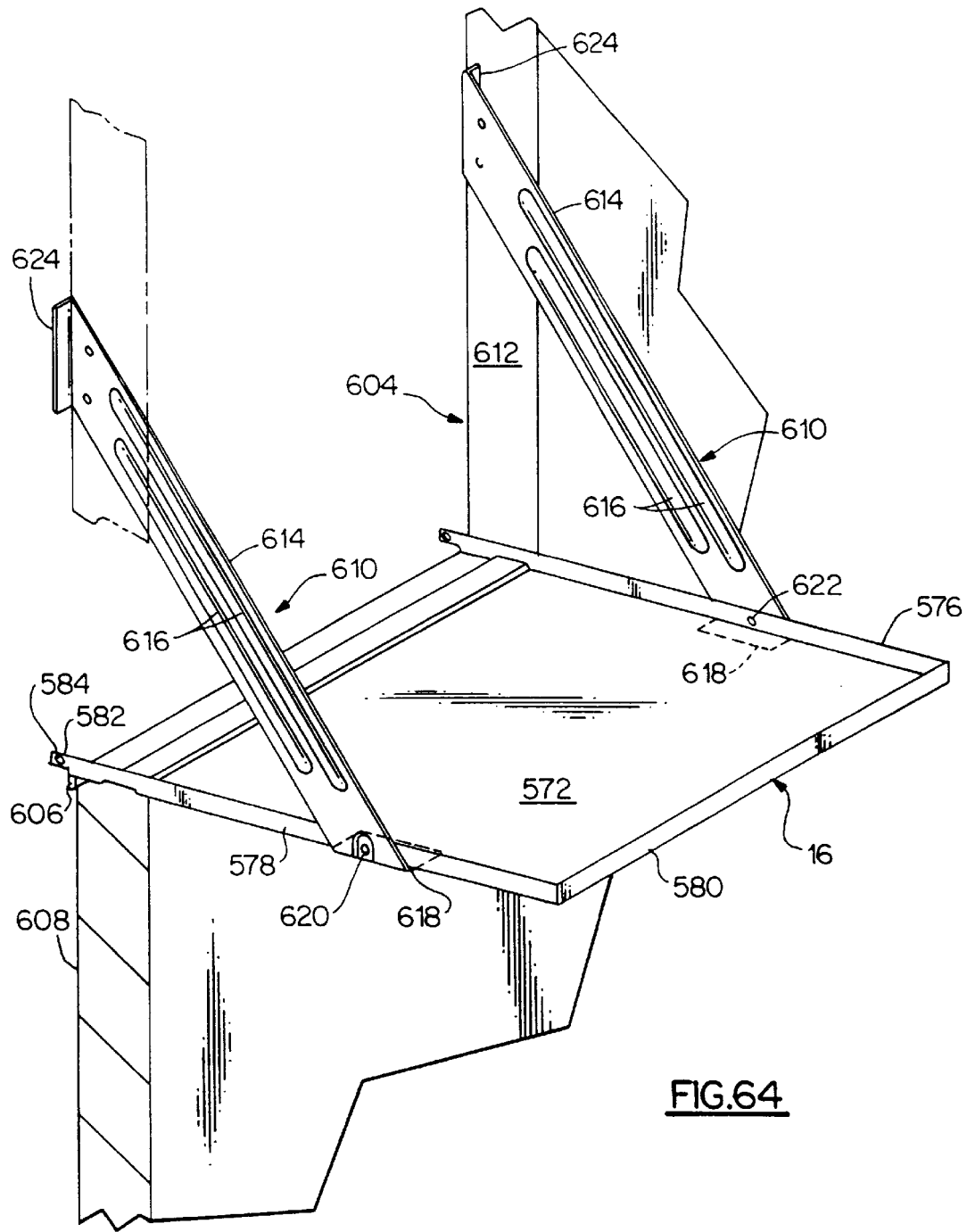
FIG. 64 is a simplified perspective view of the mounting arrangement for the room air conditioner of FIG. 1.

The assembly of the indoor and outdoor modules is then placed in the metal base pan 16 as best illustrated in FIGS. 1, 50 and 64. The base pan 16 is fabricated from structural sheet steel and comprises a substantially planar lower section 572, which has a number of structural channels 574 formed therein. The base pan 16 has vertically upstanding left and right side walls 576 and 578, respectively, and a rear wall 580 formed about the periphery thereof. These walls extend vertically a distance sufficiently to positively engage the outside walls of the air conditioning unit 10 to support the unit without interfering with air flow through any of the louvers 36 and 42. At least the right hand side wall 578 has a forwardly extending tab 582 having an opening therethrough, which is in alignment with a mating opening 586 provided in the lower right side wall 54 of the indoor housing 44. As will be seen, this connection is simply a "safety" connection to prevent movement of the air conditioning unit 10 out of the base pan during shipping and following installation, which will be described in detail below.

With the indoor and outdoor modules 12 and 14 assembled, the system of the air conditioning unit 10 for collecting condensate removed by passage of humid air through the evaporator coil 18 and conducting that condensate to the back of the outdoor module 14 will be described. Looking back now at FIGS. 24 through 26, it will be appreciated that the lower extension 150 of the scroll enclosure 90, which serves to mount the lower portion of the evaporator coil 20, also serves as the condensate drain pan for the evaporator coil when the system is used as a room air conditioner. As seen in FIG. 5, a cylindrical outlet 588 is provided at the bottom of the scroll enclosure 90 in fluid connection with the drain pan 150.

When the indoor section is assembled, the cylindrical outlet 588 is received in telescoping relationship with the outer end of the elongated hollow tube 72, which is molded into the rear wall 46 of the indoor housing as previously described and illustrated in connection with FIGS. 11 and 12. With reference to FIG. 3, the condensate drain tube exits from the rear wall 46 of the indoor housing 44 and communicates with receiving structure 590 surrounding an opening 592 in the front wall 580 of the lower outdoor housing 40, as illustrated in FIGS. 2 and 3. An appropriate sealing compound may be applied around the telescoping joints in order to assure fluid tight connections.

With continued reference to FIG. 3, the opening 592 communicates with a condensate flow channel 594 integrally formed into the lower wall 414 of the housing section 40. This channel is defined by pairs of vertically extending substantially parallel walls 596 and 598 and extends generally rearwardly to the wall 510. It then extends to the right and rearwardly around the end of the wall extension 538 to a channel 600 behind and extending parallel to the condenser coil 28. Water passing through the channel 600 is preferably blown up onto the condenser coil 28 by the action of the outdoor fan 30 to increase the efficiency of the system. Any condensate not evaporating as the result of such action will continue to the left hand end of the channel 60 and may exit from the lower housing 40 through a cylindrical exit 602.

It should be appreciated that the above described condensate removal system is designed to function simply and efficiently when the air conditioning unit 10 is used as a room air conditioner. The ability of the scroll enclosure 90 to function as a condensate drain collector when the air conditioning unit is used as a split system and the indoor module 12 is mounted with its top and bottom reversed will be described below.

A further feature of the metal base pan 16 is its ability to facilitate easy mounting of the air conditioning unit 10 through an appropriate rectangular opening 604, such as an opening in a wall or a suitably sized window. With reference now to FIG. 64 and 50, the open front end of the base pan is provided with an integrally formed longitudinally and downwardly extending alignment flange 606. Once an appropriate size opening 604 has been made, the assembly of the indoor module 12 and the outdoor module 14 is removed from the metal base pan 16 by removal of the screw in the forwardly extending tab 582. The base pan 16 is then positioned in the opening 604 with the alignment flange 606 in engagement with the inside wall 608 surrounding the opening 604. A pair of diagonally extending support channels 610, which are provided with the air conditioning unit 10, are then installed to the base pan 16 and to an inside surface 612 of the opening 604 to thereby precisely align the base pan 16 at the optimum position for support of the air conditioning unit 10.

With continued reference to FIG. 64, each of the diagonal channels 610 is formed from a structural sheet steel and includes a longitudinally extending section 614 having several reinforcing ribs 616 formed therein. The outside ends of each of the channels 610 includes a lower flange 618, which is bent inwardly to underlie and structurally support the base pan 16. The lower end of the longitudinal section 614 are provided with openings therein 620, which are in axial alignment with mating openings 622 provided in the side wall 576 and 578 of the base pan 16. Appropriate threaded fasteners (not shown) pass through the openings 620 and 622 to structurally attach the support 610 to the base pan 16.

The upper inside ends of the longitudinal section 614 of the channels are provided with outwardly bent alignment tabs 624. The length of the diagonal support channels 610 is such that when supports are attached to the base pan, as described above, and the alignment tabs 624 are in engagement with the inside wall 608, the base pan 16 is at the optimum orientation for installation and operation of the air conditioning unit 10. Accordingly, once the alignment tabs are engaged with the wall 608 appropriate fasteners, depending upon the material of the inside wall 608, are installed through openings 626 provided in the portion of the longitudinal section 614 of the channel which is in confronting relation with the faces 612 of the side wall 604.

Following installation of the support structure, as illustrated in FIGS. 64, the assembled air conditioning unit 10 may be readily slid into the base pan 16 and the attaching screw reattached through the tab 582 to thereby retain the air conditioner in its operative position. The unit may then be plugged in, turned on and the cooling and dehumidifying effects enjoyed.

As described previously, the module construction of the air conditioning unit 10 allows the indoor module 12 and the outdoor module 14 to be installed separately as a split system air conditioner. Such an installation in illustrated in FIGS. 65 and 66.

First, with respect to the outdoor section, it will be noted that no louvers are provided in the side wall 630 of the lower housing 40. In place of the louvers, an opening 632 is provided, which provides access for refrigerant tubing and electrical wiring as generally represented at reference numeral 634. The tubes and electrical wiring are shown passing through an exterior wall 636 and communicating with the indoor module 12, which is mounted on the interior wall 638 near the ceiling 640 thereof.

It will be noted that the indoor module 12 in the split system application is mounted in a top to bottom reversal from the way the indoor module 12 is on oriented in the room air conditioner application. Such installation allows the air discharge as indicated by the arrow 642 through the indoor air discharge 26 to be at the lower end of the housing as is conventional for split system air conditioners. Also, the control knobs 296, being at the lower end, are more readily accessible with the high wall mount arrangement. It should be understood that the unit may be provided with a remote control arrangement for the controls, which may be installed in place of the control box 182 and which would be actuateable by a remote control as is well known in the prior art.

All of the systems of the indoor module, as descried in detail above, are designed to be efficiently operational in the reversed orientation.

One function of the indoor module 12 in the split system application, which is different from the room air conditioning application, is the condensate disposal system. With reference now, again, to FIGS. 24 through 26, it will be recalled that the evaporator coil is supported in substantially identical horizontally extending extensions 148 and 150 at the upper and lower ends thereof. As described hereinabove, the lower extension 150 serves as the condensate drain pan when the unit is used as a room air conditioner. When the unit is used in a split system application, the condensate drain pan 148 serves as the condensate collector in a like manner. As shown in FIG. 25, an outlet 644 communicates with the condensate drain pan 148. The outlet 644 is adapted to have a condensate drain tube (not shown) attached thereto, which passes through an opening 646 provided in the rear wall 46 of the indoor housing 44, as shown in FIG. 11. From this point, the condensate drain tube may pass to an appropriate condensate disposal location as is conventional for such split system installations.

What is claimed is:

1. A subassembly of an electric motor and a fan for use in an air conditioner, said fan comprising:

a centrifugal fan adapted for rotation about a longitudinal axis, said fan having an open inlet end at one longitudinal end thereof and a convex closed end partition defining a cup shaped space at the other axial end thereof;

said motor comprising:

a housing having an axial length and a width, and a drive shaft extending from one axial end thereof;

said closed end partition having a centrally disposed axially extending opening therethrough, said drive shaft of said motor being adapted to be received in said opening and operatively attached thereto, said width of said motor housing and said cup shaped space being sized to allow a substantial portion of the said axial length of said housing to be received within said cup shaped space when said drive shaft is operably attached to said partition.

2. The apparatus of claim 1 wherein more than half of the axial length of said motor housing is received within said cup shaped space.

3. The apparatus of claim 2 wherein more than seventy-five percent (75%) of said axial length is received within said cup shaped space.

4. An evaporator module for an air conditioner comprising:

a substantially rectangular structural housing having a rear wall;

an evaporator fan and motor subassembly, said subassembly comprising:

a centrifugal fan adapted for rotation about a longitudinal axis, said fan having an open inlet end at one longitudinal end thereof and a convex closed end partition defining a cup shaped space at the other axial end thereof;

said motor comprising:

a housing having an axial length and a width, and a drive shaft extending from one axial end thereof, said motor including fan motor mounting structure extending about the periphery thereof;

said closed end partition having a centrally disposed axially extending opening therethrough, said drive shaft of said motor being adapted to be received in said opening and operatively attached thereto, said width of said motor housing and said cup shaped space being sized to allow a substantial portion of the said axial length of said housing to be received within said cup shaped space when said drive shaft is operably attached to said partition;

wherein said rear wall of said housing is provided with an axially aligned opening therein which is adapted to receive at least a portion of said fan motor therein;

said rear wall further having fan support structure associated therewith which defines said opening, said fan support structure adapted to extend into said cup shaped space to engage said fan motor mounting support structure to support said fan and motor subassembly in its desired operative position with respect to said housing.

5. The apparatus of claim 4 wherein said fan support structure comprises a cylindrical extension from said rear wall of said housing smaller in diameter than at least a portion of said cup shaped space and larger in diameter than said width of said motor housing, said cylindrical extension carrying motor attachment structure at its end extending into said cup shaped space; and wherein said fan motor mounting device engages said mounting structure in a snap lock manner without requiring additional fasteners.

6. The apparatus of claim 5 wherein said fan motor mounting device comprises:

a circumferentially extending flange on said motor housing, said flange including plurality of radially outwardly extending lugs; and wherein said fan engaging structure on said cylindrical extension comprise mating recesses adapted to receive each of said lugs into a snap fit relationship.

7. The apparatus of claim 6 further including a vibration isolating insert surrounding each of said lugs prior to engagement with said mating structure.

\* \* \* \* \*